(12) United States Patent
Ainsworth et al.

(10) Patent No.: US 8,747,472 B2
(45) Date of Patent: Jun. 10, 2014

(54) SPINAL THERAPY DEVICE WITH FIXATED DISTRACTION DISTANCE

(75) Inventors: Stephen D. Ainsworth, Wilmington, NC (US); Leighton J. LaPierre, Wilmington, NC (US)

(73) Assignee: Baxano Surgical, Inc., Raleigh, NC (US)

(*) Notice: Subject to any disclaimer, the term of this patent is extended or adjusted under 35 U.S.C. 154(b) by 730 days.

(21) Appl. No.: 12/541,785

(22) Filed: Aug. 14, 2009

(65) Prior Publication Data

US 2011/0040329 A1 Feb. 17, 2011

(51) Int. Cl.
*A61F 2/44* (2006.01)

(52) U.S. Cl.
USPC ........ 623/17.11; 606/320; 606/326; 606/328; 606/105

(58) Field of Classification Search
USPC .............. 623/17.11–17.16; 606/90, 105, 246, 606/247, 258, 259, 261, 300, 320, 328, 606/301–317, 318, 319, 326, 327, 251, 63, 606/68; 411/384
See application file for complete search history.

(56) References Cited

U.S. PATENT DOCUMENTS

| | | | |
|---|---|---|---|
| 640,661 A | 1/1900 | Johnstone | |
| 1,029,104 A | 6/1912 | Clark | |
| 1,079,224 A | 11/1913 | Dodds | |
| 1,086,144 A | 2/1914 | Dodds | |
| 1,111,691 A | 9/1914 | Flannery | |
| 3,272,541 A | 9/1966 | Latzen | |
| 3,367,326 A | 2/1968 | Frazier | |
| 3,892,232 A | 7/1975 | Neufeld | |
| 4,175,555 A | 11/1979 | Herbert | |
| 4,297,047 A | 10/1981 | Farrant | |
| 4,309,777 A | 1/1982 | Patil | |
| 4,553,273 A | 11/1985 | Wu | |
| 4,554,914 A | 11/1985 | Kapp et al. | |
| 4,573,448 A | 3/1986 | Kambin | |
| 4,636,217 A | 1/1987 | Ogilvie et al. | |
| 4,657,550 A | 4/1987 | Daher | |
| 4,858,601 A | 8/1989 | Glisson | |
| 4,862,891 A | 9/1989 | Smith | |
| 4,875,794 A | 10/1989 | Kern, Jr. | |
| 4,932,925 A | 6/1990 | Roinestad et al. | |
| 4,932,975 A | 6/1990 | Main et al. | |
| 4,969,888 A | 11/1990 | Scholten et al. | |
| 5,002,546 A | 3/1991 | Romano | |
| 5,019,080 A * | 5/1991 | Hemer | 606/104 |

(Continued)

OTHER PUBLICATIONS

Rathke/Schlegel—surgery of the spine —Atlas of Orthopedic Operations, vol. 1,—1979 —pp. 222-224.

(Continued)

*Primary Examiner* — Jan Christopher Merene
*Assistant Examiner* — Atiya Mahmud
(74) *Attorney, Agent, or Firm* — Kevin E. Flynn; Flynn IP Law

(57) ABSTRACT

Assemblies for implantation across one or more spinal motion segments to allow for control of the distance between bone anchors. Control of distance between bone anchors may be provided by one inter-anchor element pushing the pair of bone anchors apart and a second inter-anchor element pulling the pair of bone anchors together. Control of distance between bone anchors may be provided through use of dissimilar thread pitch. Compression of intervertebral disc space through controlled movement of a pair of anchored bone anchors towards one another.

36 Claims, 27 Drawing Sheets

(56) References Cited

U.S. PATENT DOCUMENTS

| | | | | |
|---|---|---|---|---|
| 5,078,718 | A | 1/1992 | Moll et al. | |
| 5,246,458 | A | 9/1993 | Graham | |
| 5,336,223 | A * | 8/1994 | Rogers | 606/258 |
| 5,360,430 | A | 11/1994 | Lin | |
| 5,480,401 | A | 1/1996 | Navas | |
| 5,562,737 | A | 10/1996 | Graf | |
| 5,571,192 | A | 11/1996 | Schonhoffer | |
| 5,702,455 | A | 12/1997 | Saggar | |
| 5,733,284 | A | 3/1998 | Martin | |
| 5,807,318 | A | 9/1998 | St. Goar et al. | |
| 5,827,285 | A * | 10/1998 | Bramlet | 606/60 |
| 5,916,267 | A | 6/1999 | Tienboon | |
| 5,921,971 | A | 7/1999 | Agro et al. | |
| 5,935,131 | A | 8/1999 | Bonutti | |
| 5,972,015 | A | 10/1999 | Scribner et al. | |
| 5,989,290 | A | 11/1999 | Biedermann et al. | |
| 6,010,495 | A | 1/2000 | Tilton, Jr. | |
| 6,056,749 | A | 5/2000 | Kuslich | |
| 6,063,121 | A | 5/2000 | Xavier et al. | |
| 6,086,589 | A | 7/2000 | Kuslich et al. | |
| 6,093,205 | A | 7/2000 | McLeod et al. | |
| RE36,857 | E | 9/2000 | Euteneuer et al. | |
| 6,127,597 | A | 10/2000 | Beyar et al. | |
| 6,241,734 | B1 | 6/2001 | Scribner et al. | |
| 6,319,254 | B1 | 11/2001 | Giet et al. | |
| 6,383,190 | B1 | 5/2002 | Preissman | |
| 6,395,034 | B1 | 5/2002 | Suddaby | |
| 6,402,750 | B1 | 6/2002 | Atkinson et al. | |
| 6,458,134 | B1 * | 10/2002 | Songer et al. | 606/304 |
| 6,517,543 | B1 | 2/2003 | Berrevoets et al. | |
| 6,558,386 | B1 | 5/2003 | Cragg | |
| 6,558,390 | B2 | 5/2003 | Cragg | |
| 6,652,535 | B2 | 11/2003 | Kvarnstrom et al. | |
| 6,669,699 | B2 | 12/2003 | Ralph et al. | |
| 6,692,495 | B1 | 2/2004 | Zacouto | |
| 6,764,489 | B2 | 7/2004 | Ferree | |
| 6,790,210 | B1 | 9/2004 | Cragg et al. | |
| 6,805,697 | B1 | 10/2004 | Helm et al. | |
| 6,899,716 | B2 | 5/2005 | Cragg | |
| 7,166,107 | B2 * | 1/2007 | Anderson | 606/86 A |
| 7,175,626 | B2 * | 2/2007 | Neff | 606/86 A |
| 7,255,714 | B2 | 8/2007 | Malek | |
| 7,361,192 | B2 | 4/2008 | Doty | |
| 7,419,505 | B2 | 9/2008 | Fleischmann et al. | |
| 7,547,324 | B2 | 6/2009 | Cragg et al. | 623/17.11 |
| 8,343,201 | B2 * | 1/2013 | Biyani et al. | 606/318 |
| 2002/0161444 | A1 * | 10/2002 | Choi | 623/17.11 |
| 2003/0055427 | A1 | 3/2003 | Graf | |
| 2003/0181982 | A1 | 9/2003 | Kuslich | |
| 2004/0210227 | A1 * | 10/2004 | Trail et al. | 606/73 |
| 2005/0113919 | A1 * | 5/2005 | Cragg et al. | 623/17.11 |
| 2005/0261695 | A1 | 11/2005 | Cragg et al. | |
| 2006/0052788 | A1 * | 3/2006 | Thelen et al. | 606/72 |
| 2006/0058800 | A1 * | 3/2006 | Ainsworth et al. | 606/72 |
| 2006/0079898 | A1 * | 4/2006 | Ainsworth et al. | 606/61 |
| 2006/0229609 | A1 | 10/2006 | Wang | |
| 2007/0106383 | A1 | 5/2007 | Abdou | |
| 2007/0168036 | A1 * | 7/2007 | Ainsworth et al. | 623/17.13 |
| 2007/0270855 | A1 * | 11/2007 | Partin | 606/72 |
| 2008/0140207 | A1 * | 6/2008 | Olmos et al. | 623/17.16 |
| 2008/0177291 | A1 * | 7/2008 | Jensen et al. | 606/151 |
| 2008/0195156 | A1 | 8/2008 | Ainsworth et al. | 606/279 |
| 2009/0005782 | A1 * | 1/2009 | Chirico et al. | 606/63 |
| 2009/0105768 | A1 | 4/2009 | Cragg et al. | 606/301 |
| 2009/0248089 | A1 * | 10/2009 | Jacofsky et al. | 606/311 |
| 2010/0228301 | A1 * | 9/2010 | Greenhalgh et al. | 606/313 |
| 2010/0274357 | A1 * | 10/2010 | Miller et al. | 623/17.16 |

OTHER PUBLICATIONS

International Search Report and Written Opinion From Corresponding PCT Application No. PCT/US2010/045135, Oct. 6, 2010 (15 pgs).

* cited by examiner

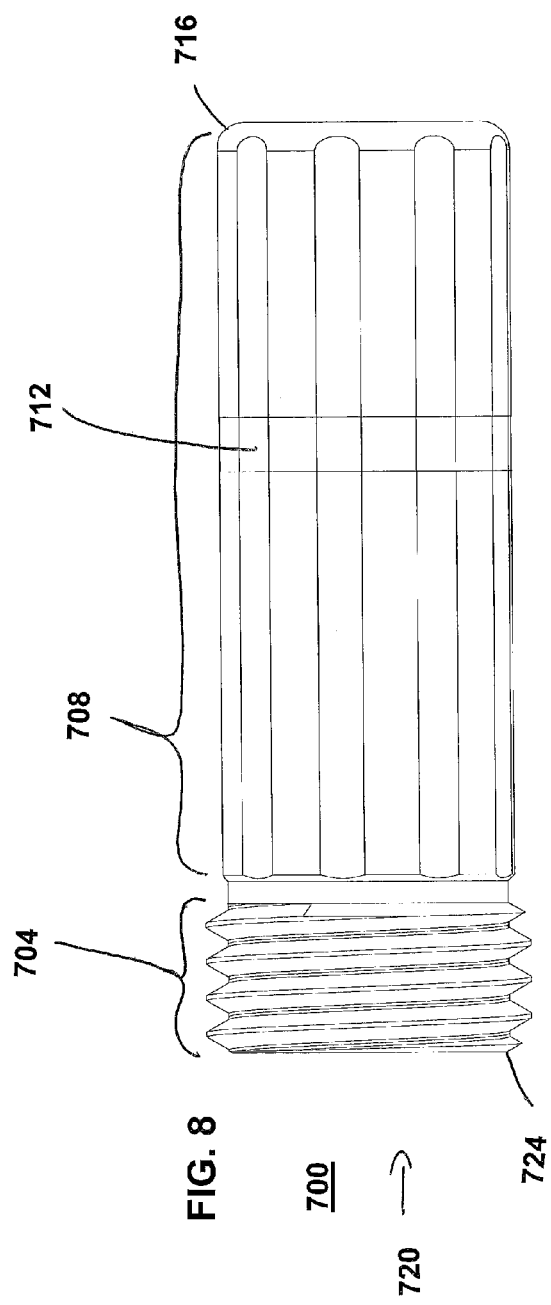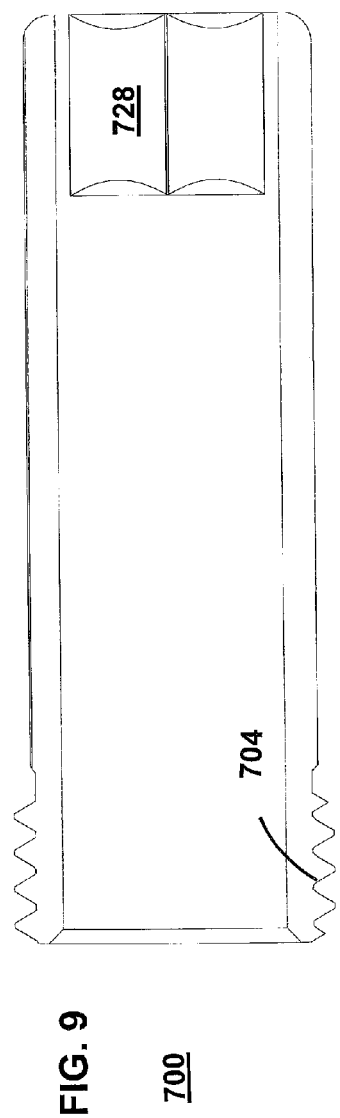

SPINAL THERAPY DEVICE WITH FIXATED DISTRACTION DISTANCE

BACKGROUND

1. Field of the Disclosure

The present disclosure relates generally to implantable device assemblies, instrumentation systems, and methods for accessing and treating multiple levels of the lumbar spine via a minimally-invasive trans-sacral approach (as described in U.S. Pat. No. 6,558,390 which is incorporated herein by reference). More specifically, in one aspect of the disclosure, the present disclosure generally relates to the imposition of a sequence of two or more distractions on a set of two or more adjacent motion segments as part of the provision of therapy to the spine. The therapy may include an objective to stabilize a portion of the spine and may further include using fusion as part of that stabilization.

The distraction process involves setting a minimum distance between a pair of bone anchors and then locking the bone anchors together to prevent the bone anchors from moving beyond that minimum distance between the bone anchors. One set of teachings within the disclosure teaches a way to compress the distance between two adjacent vertebrae by pulling the bone anchors in the two vertebrae towards each other to provide control over the final distraction distance between the vertebrae and to allow for the imposition of compression of the material placed between the vertebrae.

2. Background Information and Related Art

The concept of providing therapy to adjacent motion segments including fusion therapy is addressed in co-pending and commonly assigned U.S. patent application Ser. No. 11/202,655 for Methods and Apparatus for Provision of Therapy to Adjacent Motion Segments published Mar. 16, 2006 as U.S. Pub. No. 2006/0058800 A1 and incorporated by reference herein.

The individual motion segments within the spinal columns allow movement within constrained limits and provide protection for the spinal cord. A motion segment includes two adjacent vertebrae and the disc between them. The discs are important to allow the spinal column to be flexible and to bear the large forces that pass through the spinal column as a person walks, bends, lifts, or otherwise moves. Unfortunately, for a number of reasons referenced in the '655 application, for some people one or more discs in the spinal column will not operate as intended. The reasons for disc problems range from a congenital defect, disease, injury, or degeneration attributable to aging. Often when the discs are not operating properly, the gap between adjacent vertebral bodies is reduced and this reduction in distance causes additional problems including pain.

A range of therapies have been developed to alleviate the pain associated with disc problems. One class of solutions is to remove the failed disc and then fuse the two adjacent vertebral bodies together with a permanent but inflexible spacing, also referred to as static stabilization. Fusing one section together ends the ability to flex in that motion segment. However, as each motion segment only contributes a small portion of the overall flexibility of the spine, it can be a reasonable trade-off to give up the flexibility of a motion segment in an effort to alleviate significant back pain.

Fusion is one type of stabilization. Other forms of stabilization may be used to alter the relative positions of components. Generally, one of the first steps in trying to provide stabilization therapy including fusion therapy is to move adjacent vertebral bodies relative to one another (called distraction) to compensate for the reduction of intervertebral space attributed to the problems with the disc. Depending on the type of therapy that is to be delivered, it may be useful to separate the adjacent vertebral bodies by more than a normal amount of separation.

3. Vocabulary

It is useful to set forth some of the standard medical vocabulary before getting into a more detailed discussion of the background of the present invention. In the context of this discussion: anterior refers to in front of the spinal column (ventral); and posterior refers to behind the column (dorsal); cephalad means towards the patient's head (sometimes "superior"); caudal (sometimes "inferior") refers to the direction or location that is closer to the feet.

As the present application contemplates accessing the various vertebral bodies and intervertebral spaces through a preferred approach that comes in from the sacrum and moves towards the head, proximal and distal are defined in context of this approach. Consequently, proximal is closer to the beginning of the channel and the surgeon's hand outside the channel and thus towards the sacrum of the patient. Distal is further from the beginning of the channel and the surgeon and thus towards the head of the patient.

While the general concept of distraction can be applied for moving one item apart from another in any dimension, in the context of this application and the claims that follow, distraction is considered in the orientation of the axes of the spinal column so that distraction increases the distance between two adjacent vertebral bodies as measured in the direction of the cephalad/caudal axis of the spine.

One of skill in the art will recognize that a separate process known as subsidence may cause movement of the anchors and the components attached to the anchor relative to the vertebral body that holds the anchor. In some instances, the distance between intervertebral bodies may move due to subsidence or analogous process. From another viewpoint, the distraction between adjacent vertebrae goes to zero when the fusion process connects the two vertebrae together so there is no longer an intervertebral disc space. Thus, when this application refers to fixation of the distraction distance, all that can be controlled with certainty is the distance between the relevant anchors.

The disclosure addresses the controlled movement of bone anchors to either move them further apart from one another or move them closer together. One of skill in the art will recognize that unless otherwise specified explicitly, that motion of anchors will be relative motion that is a mere statement that the anchors are getting closer together or further apart. Thus if one anchor is pulled towards another it means that the relative distance between the two anchors is reduced. It does not mean that one anchor needs to be stationary and one anchor needs to do all the moving or that both anchors are moving relative to some external point of reference. The specific allocation of which anchor is moving relative to an external point of reference such as the operating table may be influenced by other factors such as how the patient is positioned and held on the operating table.

SUMMARY OF THE DISCLOSURE

Aspects of the teachings contained within this disclosure are addressed in the claims submitted with this application upon filing. Rather than adding redundant restatements of the contents of each of the claims, these claims should be considered incorporated by reference into this summary.

One set of teachings may be summarized by:

A method for controlling a distance between two bone anchors, the method comprising: implanting a distal bone anchor in a distal vertebral body; implanting a proximal bone anchor in a proximal vertebral body, the proximal vertebral body adjacent to and proximal to the distal vertebral body; threadedly engaging a first inter-anchor element with an interior bore within the proximal bone anchor and threadedly advancing the first inter-anchor element distally within the proximal bone anchor to cause a distal portion of the first inter-anchor element to push against the distal bone anchor; inserting a threaded portion of a second inter-anchor element through a channel within the first inter-anchor element and engaging a threaded section of an interior of the distal bone anchor; and threadedly advancing the second inter-anchor element in a distal direction within the distal bone anchor to pull the proximal bone anchor towards the distal bone anchor until the distance between the distal bone anchor and the proximal bone anchor is fixed.

Another set of teachings may be summarized by:

A method for setting a distance between a proximal bone anchor and a distal bone anchor in adjacent vertebral bodies; the method comprising: rotating a first inter-anchor element threadedly engaged with the pair of bone anchors to use dissimilar thread pitch to set the distance between the pair of bone anchors.

Another set of teachings may be summarized by compressing the contents of an intervertebral disc space through reduction of the distance between anchored bone anchors. The intervertebral disc space may be merely compressed from the pre-therapy height of the disc space or the disc space may have been temporarily hyper-distracted before the compression.

Another set of teachings may be summarized by creation of an assembly for implantation across two spinal vertebrae comprising: a distal anchor for engagement with a distal vertebra; a proximal anchor for engagement with a proximal vertebra; and a retraction inducing element adapted to engage a shoulder within an interior of the proximal anchor and to engage an interior of the distal anchor such that rotation of the compression inducing element has a capacity to reduce a distance between the distal anchor and the proximal anchor.

Another set of teachings may be summarized as the fabrication of the components and assembly of completed combinations of components shown in the various drawings.

This summary is meant to provide an introduction to the concepts that are disclosed within the specification without being an exhaustive list of the many teachings and variations upon those teachings that are provided in the extended discussion within this disclosure. Thus, the contents of this summary should not be used to limit the scope of the claims that follow.

Inventive concepts are illustrated in a series of examples, some examples showing more than one inventive concept. Individual inventive concepts can be implemented without implementing all details provided in a particular example. It is not necessary to provide examples of every possible combination of the inventive concepts provided below as one of skill in the art will recognize that inventive concepts illustrated in various examples can be combined together in order to address a specific application.

Other systems, methods, features, and advantages of the disclosed teachings will be or will become apparent to one with skill in the art upon examination of the following figures and detailed description. It is intended that all such additional systems, methods, features and advantages be included within the scope of and be protected by the accompanying claims.

BRIEF DESCRIPTION OF THE FIGURES

The disclosure can be better understood with reference to the following figures. The components in the figures are not necessarily to scale, emphasis instead being placed upon illustrating the principles of the disclosure. Moreover, in the figures, like reference numerals designate corresponding parts throughout the different views.

FIG. 8 provides a side view of a spanning distraction rod.

FIG. 9 is a cross section of FIG. 8 and shows a driver engagement section.

DETAILED DESCRIPTION

Figure 1:
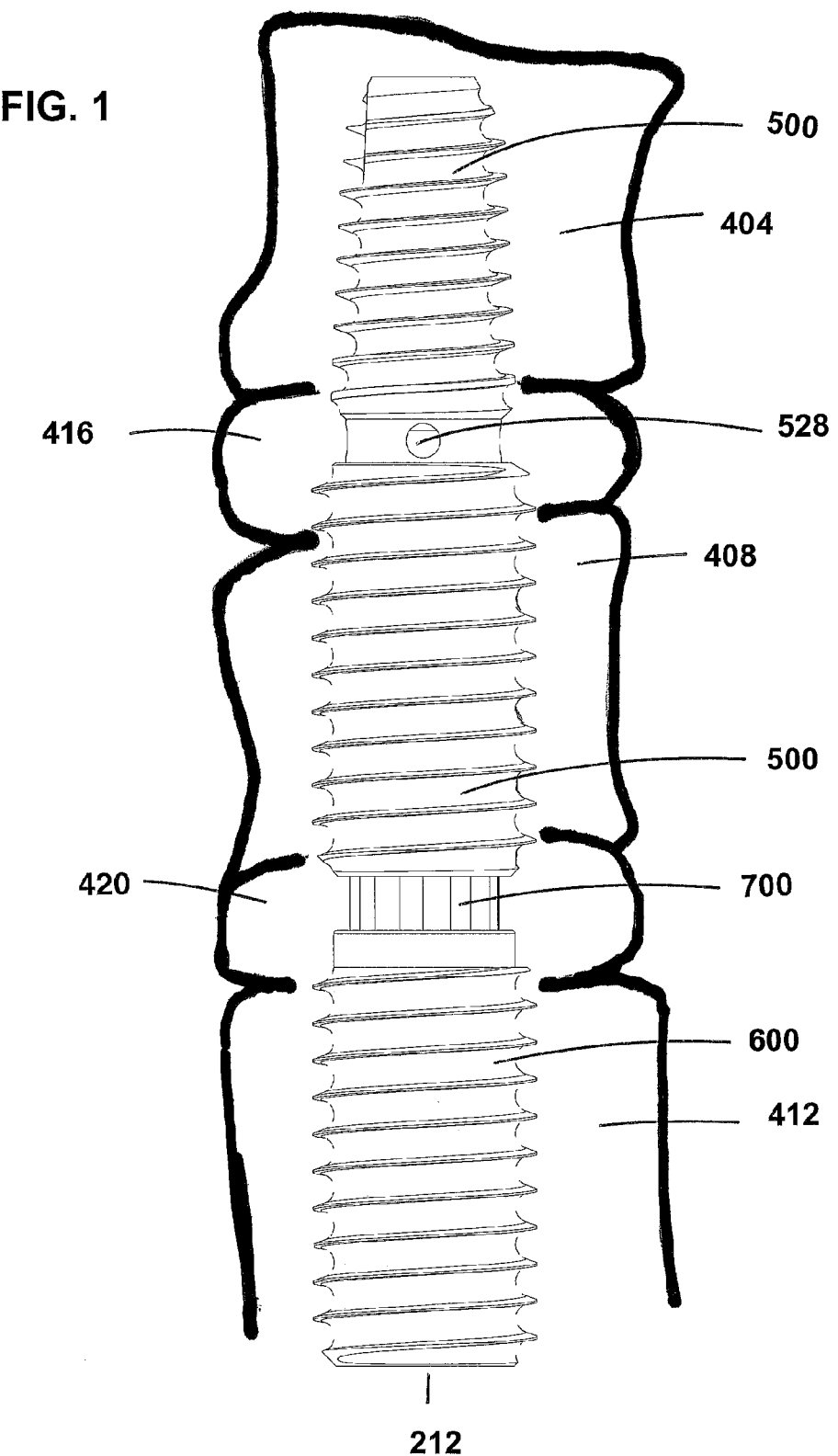
FIG. 1 shows a lateral view of a portion of a human spine with a two-level fusion assembly connected to three vertebrae and traversing two adjacent intervertebral disc spaces.

FIG. 1 shows a lateral view of a portion of a human spine with a two-level fusion assembly 100 connected to three vertebrae and traversing two adjacent intervertebral disc spaces. FIG. 1 omits the biological structures of the spine not relevant to the present disclosure.

The three vertebrae may be called, the distal vertebral body 404 (or the distal vertebra), medial vertebral body 408 (or the medial vertebra), and proximal vertebral body 412 (or the proximal vertebra). The intervertebral space between the distal vertebral body 404 and the medial vertebral body 408 may be called the distal intervertebral disc space 416. Likewise the intervertebral space between the medial vertebral body 408 and the proximal vertebral body 412 may be called the proximal intervertebral disc space 420. In a trans-sacral procedure, the access channel 212 for the preparation and implantation is accessed from the sacrum located at the caudal end of the spine and thus the concepts of proximal and distal are taken with respect to the trans-sacral access.

The three vertebrae may be the L4, L5, and S1 vertebrae. The S1 vertebra is the top portion of the sacrum which is fused from several individual components including S1. The teachings of the present disclosure may be used in other pairs of motion segments and thus the three vertebrae represented in FIG. 1 may be L3, L4, and L5 or possibly an even more cephalad pair of adjacent motion segments. One of skill in the art will recognize that three or more adjacent motion segments could be provided therapy such that there would be more than one medial vertebra and more than two treated intervertebral disc spaces.

Various details of the two-level fusion assembly are visible in FIG. 1. The major components described in greater detail below are the fusion rod 500, proximal anchor 600, and a portion of spanning distraction rod 700. As described below, a small portion of the fixation rod 800 (not labeled in FIG. 1) is visible through the set of ports 528.

Figure 2:
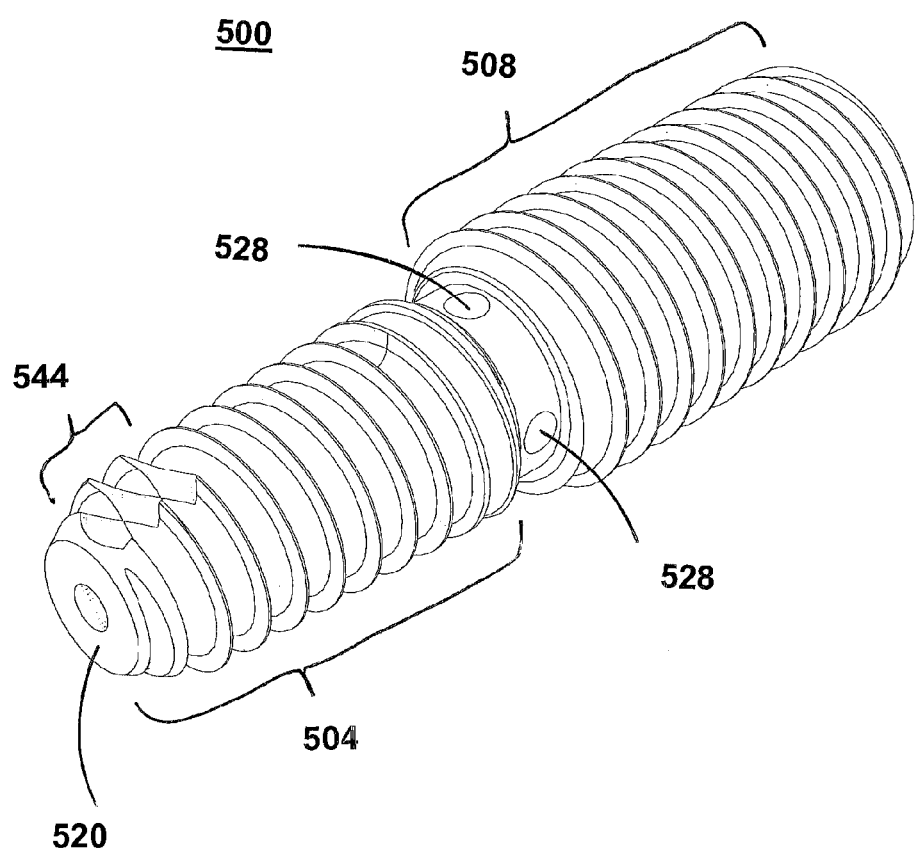
FIG. 2 is an isometric view of a fusion rod.
Figure 3:
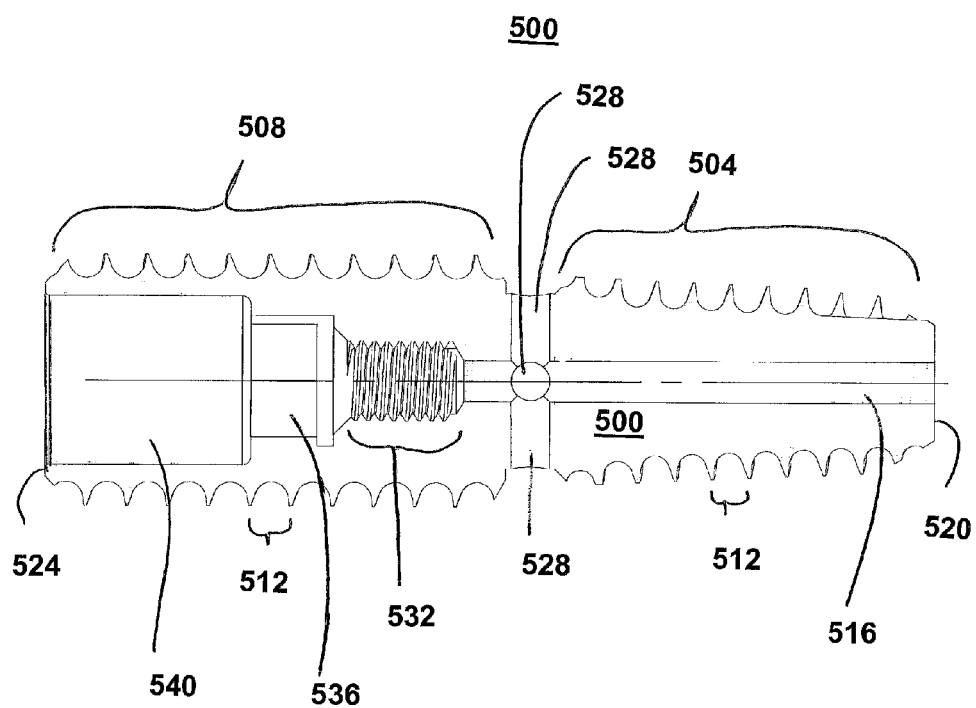
FIG. 3 is a cross section of FIG. 2.

FIG. 2 and FIG. 3 show a fusion rod 500 with a distal thread 504 and a proximal thread 508. The proximal and distal threads 504 and 508 may be placed substantially in two adjacent vertebrae. (Note while a view of a threaded rod in cross section appears to have a set of threads, typically there is one helical thread that travels over the surface of the threaded rod). Because of the significant differences in the major diameters of the two threads, the two threads may have different thread pitches without a risk of cross-threading or a need for timed delivery. Thread pitch, as used herein, is the distance between corresponding points on a thread. This concept is easy to see in a cross section such as FIG. 3 and is shown by distance 512. The thread pitch of the distal thread 504 is the same as the thread pitch of the proximal thread 508. Thread pitch is frequently described in terms of threads per inch or TPI.

While the example of the fusion rod 500 shown in FIG. 2 and FIG. 3 uses the same thread pitch for the distal thread 504 and the proximal thread 508, dissimilar thread pitches may be used in order to provide distraction.

Use of Dissimilar Thread Pitch in Fusion Rod

The use of dissimilar thread pitches to distract vertebral bodies within a single motion segment is described in commonly assigned U.S. Pat. No. 6,921,403 "Method and Apparatus for Spinal Distraction and Fusion" issued on Jul. 26, 2005 filed on that same date, which are herein incorporated in their entirety by reference into this disclosure.

Dissimilar thread pitch may be used to provide a predictable amount of distraction of a motion segment as the distraction is a function of the ratio of the thread pitches. For example if the distal thread has a pitch of 12 thread peaks per inch (typically called threads per inch) and the proximal thread has a pitch of 10 thread peaks per inch, then when the rod is engaged with the two adjacent vertebrae, distraction will occur during rotation of the rod. More specifically, when the rod is rotated in the appropriate direction for the handedness of the threads, the rod will move distally 1 inch into the distal vertebra with 12 rotations of the rod driver. However, these same 12 rotations of the rod driver will advance the rod relative to the proximal vertebra 1.2 inches. Thus, the distance between the two vertebrae will be increased 0.2 inches.

All other things being kept equal, choosing a larger difference in thread pitch makes it possible to produce a larger amount of distraction.

Fusion rod 500 has a channel 516 that runs from the distal end 520 to the proximal end 524 and may be used to deliver the fusion rod 500 over a guide wire. The channel 516 is connected to a set of ports 528 which may be used to deliver material to a disc space.

Fusion rod 500 has an interior threaded section 532, a driver engagement section 536, and a cylindrical section 540.

FIG. 2 and FIG. 3 shows the distal thread 504 increases in major diameter from the distal end 520 towards the ports 528. A chip breaking section 544 is visible towards the distal end of the distal thread 504.

Figure 4:
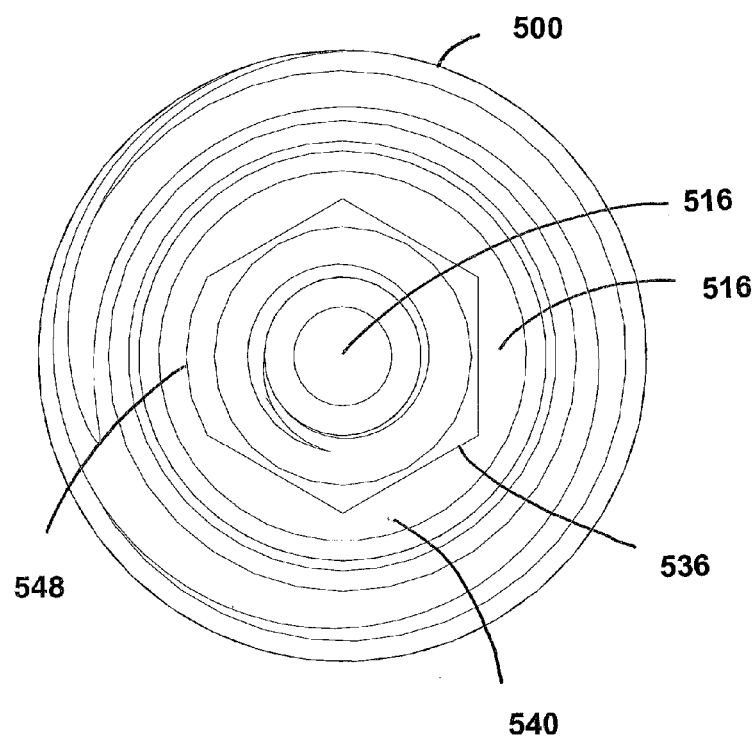
FIG. 4 is a view of the proximal end of the fusion rod.

FIG. 4 shows the channel 516 as viewed from the proximal end 524 (FIG. 3) of the fusion rod 500. Note that the driver engagement section 536 is not symmetric as one face 548 of the six faces of the substantially hexagonal opening is rounded rather than flat. The purpose of face 548 will be discussed below.

Proximal Anchor

Figure 5:
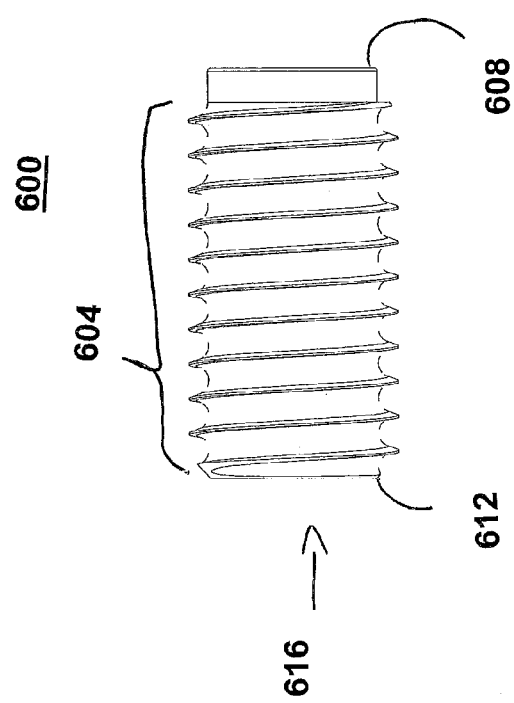
FIG. 5 is a side view of a proximal anchor.

FIG. 5 shows a proximal anchor 600. The proximal anchor 600 has an external thread 604. The proximal anchor 600 has a channel 616 that runs from the proximal end 612 to the distal end 608.

Figure 6:
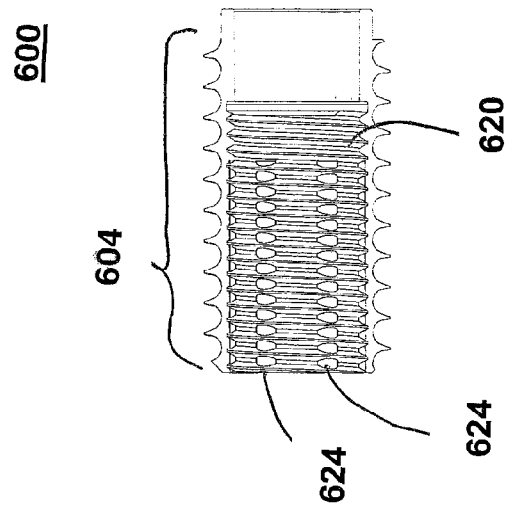
FIG. 6 is a cross section view of FIG. 5.

FIG. 6 is a cross section of FIG. 5. The cross section shows internal thread 620 and a set of notches 624 in the internal thread 620.

Figure 7:
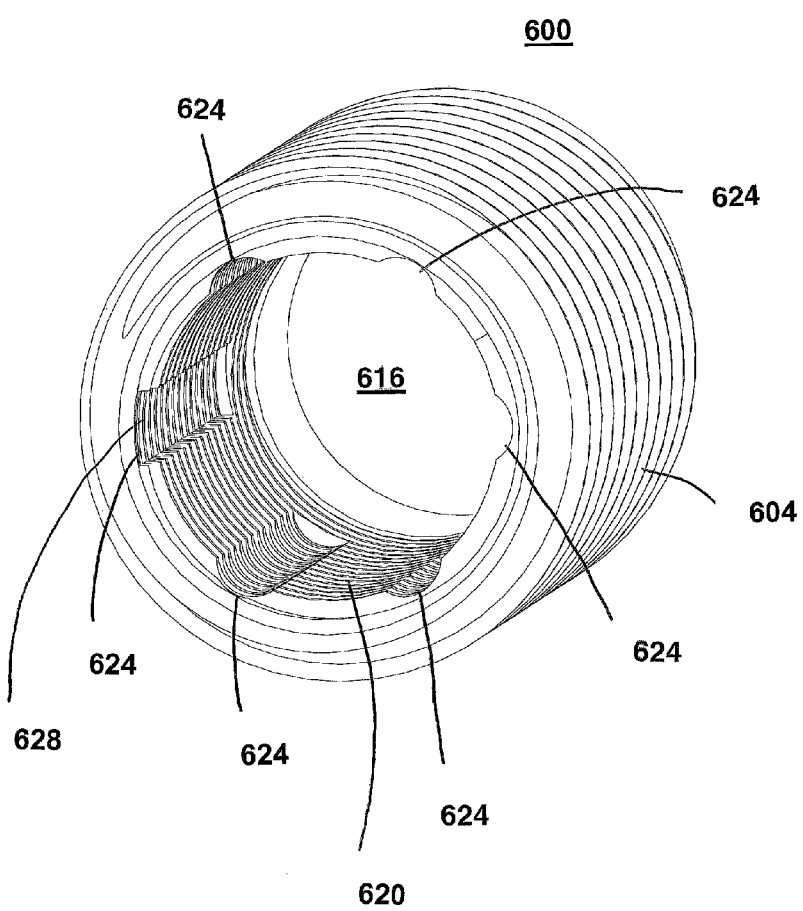
FIG. 7 is a perspective view of proximal anchor looking from the proximal end towards the distal end.

FIG. 7 is a perspective view of proximal anchor 600 looking from the proximal end towards the distal end. Internal thread 620 is visible as are the sets of notches 624. Note that one set of notches, 628, is a different shape from the other sets of notches. The notch set 628 and face 548 (FIG. 4) of the fusion rod 500 (FIG. 4) may be used to align the fusion rod 500 and the proximal anchor 600 on a common driver so that the two components may be delivered by timed delivery so that the external thread 604 may be sized with the same major diameter and thread pitch as the proximal thread 508 on the fusion rod 500. Timed delivery allows the second thread to travel in the thread path created by an earlier thread and do so without cross threading.

Spanning Distraction Rod

FIG. 8 provides a side view of a spanning distraction rod 700. External thread 704 is located near the proximal end 724. Distal portion 708 is shown with optional flutes (discussed below). The spanning distraction rod 700 has a channel 720 that runs through the spanning distraction rod 700 from proximal end 724 to distal end 716.

Optional band 712 may be used to provide a visual indicator for use in the process of assembling components for delivery by a driver in order to prevent the spanning distraction rod 700 from altering the spacing between the fusion rod 500 and the proximal anchor 600 on the dual driver as this would alter the timing of the threads between the two anchors. The band 712 may be a different color or texture than other portions of the distal portion 708.

FIG. 9 is a cross section of FIG. 8 and shows a driver engagement section 728.

Figure 10:
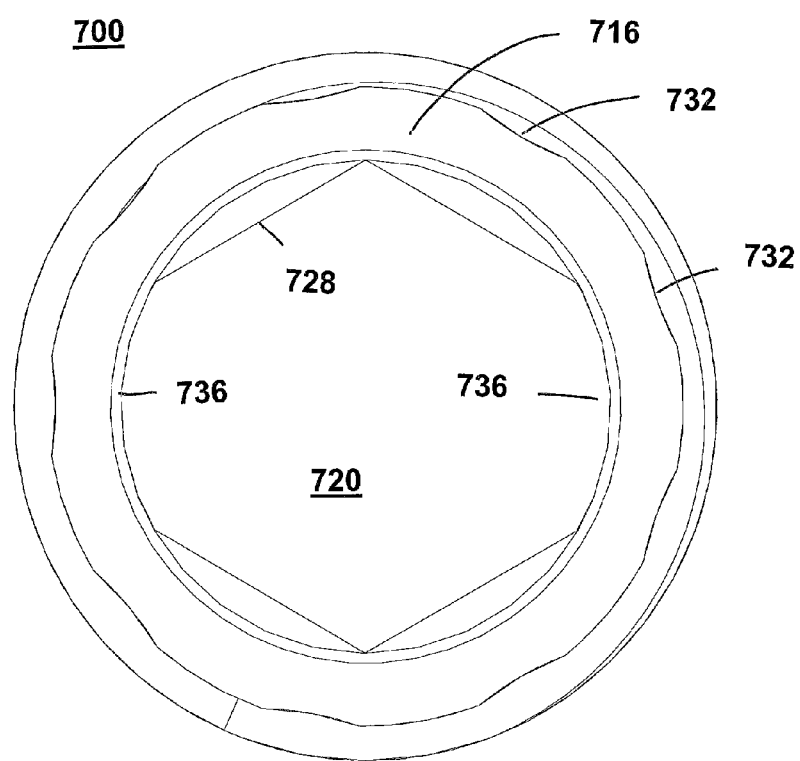
FIG. 10 shows a distal end view looking towards the proximal end of the spanning distraction rod.

FIG. 10 shows a distal end view looking towards the proximal end of the spanning distraction rod 700. The driver engagement section 728 is visible within channel 720 surrounded by the rounded distal end 716. The driver engagement section is substantially a hexagonal socket but two faces 736 are round rather than flat.

Comparing FIG. 10 to FIG. 4, one can see that a driver may be made with a single rounded face that would engage both spanning distraction rod 700 and fusion rod 500. However a second driver head with two rounded faces would drive only the spanning distraction rod 700 but not the fusion rod 500.

Returning to FIG. 10, the set of flutes 732 is visible. Fluting the distal portion 708 (FIG. 8) of spanning distraction rod 700 reduces the amount of surface area to make contact between the spanning distraction rod 700 and the internal walls of the fusion rod 500. Thus, the fluted distal portion 708 (FIG. 8) of the spanning distraction rod 700 may be rotated relative to an implanted fusion rod 500 while reducing the risk of inadvertently rotating the fusion rod 500 and changing the position of the fusion rod 500 relative to the distal vertebral body 404 (see FIG. 1) and the medial vertebral body 408 (FIG. 1). Avoiding unintended rotation of the fusion rod 500 is particularly desirable for fusion rods with dissimilar thread pitch as rotation causes a change in distraction of the distal motion intervertebral space 416 (see FIG. 1).

Fixation Rod

Figure 11:
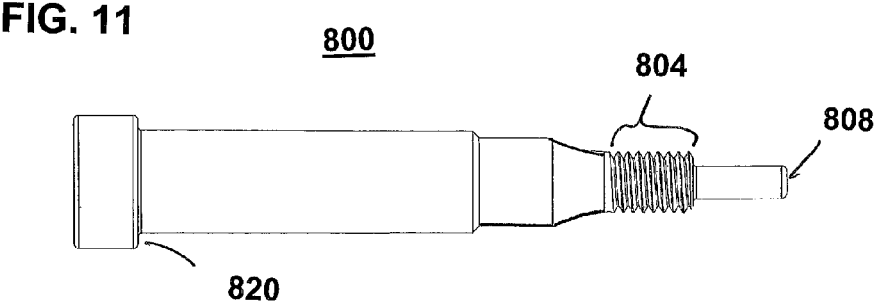
FIG. 11 is a side view of a fixation rod.
Figure 12:
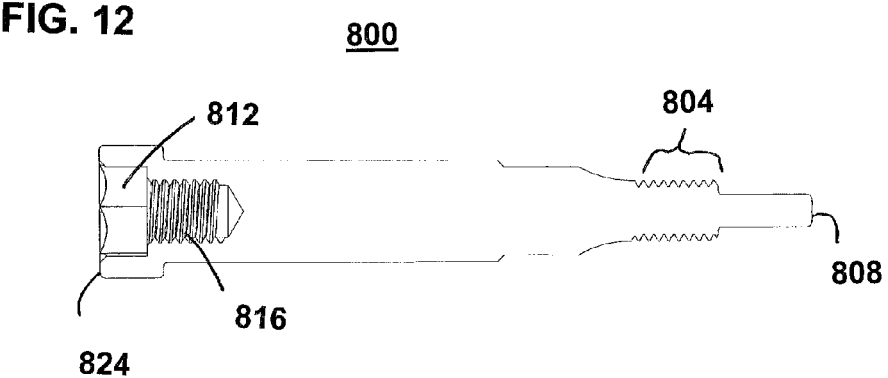
FIG. 12 is a cross section of FIG. 11.

FIG. 11 is a side view of a fixation rod 800. FIG. 12 is a cross section of FIG. 11. Fixation rod 800 has an external thread 804 near the distal end 808. A driver engagement section 812 is open at the proximal end 824 of the fixation rod 800. The driver engagement section 812 may be combined with an internal threaded bore 816 for use with a threaded retention rod in an appropriate driver to retain the fixation rod 800 to the driver. The fixation rod 800 has a shoulder 820 near the proximal end to engage a corresponding feature at the proximal end 724 of the spanning distraction rod 700 (FIG. 8).

Setting the Minimum Distance Between Vertebrae

Figure 13:
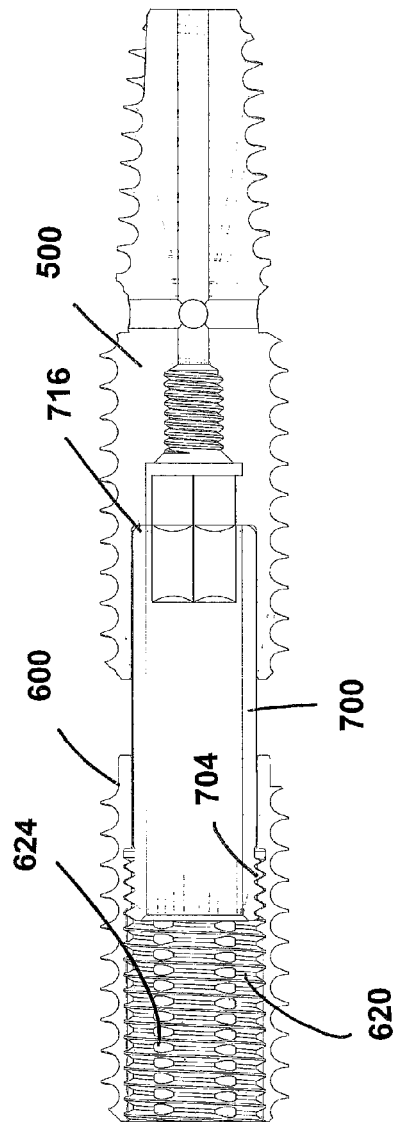
FIG. 13 is a cross section of partial assembly that includes the fusion rod, the proximal anchor, and the spanning distraction rod.

FIG. 13 is a cross section of partial assembly that includes the fusion rod 500, the proximal anchor 600, and the spanning distraction rod 700. Referencing now FIG. 1 and FIG. 13, these three components may be delivered simultaneously by one common driver into an access channel 212 that has been prepared including packing the proximal intervertebral disc space with bone chips and other fusion promoting material. Engagement of the sets of notches 624 accessible from the proximal end of the proximal anchor 600 can preclude unintentional rotation and advancement of the proximal anchor 600 relative to the proximal vertebral body 412. An appropriate driver may be used to advance the spanning distraction rod 700 relative to the proximal anchor 600 using threaded engagement of the threaded section 704 of the spanning distraction rod 700 with the internal thread 620 in the proximal anchor 600.

Rotation and advancement in the distal direction of the spanning distraction rod 700 causes the rounded distal end 716 to contact the fusion rod 500 and to push the fusion rod 500 to increase the distance between the proximal vertebral body 412 anchored to the proximal anchor 600 and the medial vertebral body 408 anchored to the fusion rod 500. Selection of components of known lengths and arrangements allows the movement of the spanning distraction rod to be a means for increasing distraction of an intervertebral space by setting a minimum distance between the proximal anchor 600 and the fusion rod 500 and thus allows for the controlled increase in the space between the proximal vertebral body 412 and the medial vertebral body 408.

Reducing the Intervertebral Disc Space Height

Sometimes a surgeon may advance the spanning distraction rod 700 to impose a first distraction and after evaluation of the fluoroscopic images, may decide that a decrease in imposed distraction is appropriate. While not a frequent occurrence, a surgeon may want to decrease the height of an intervertebral disc space from the pre-surgery height. In either case, the surgeon is looking to reduce the height of the intervertebral disc space.

Figure 14:
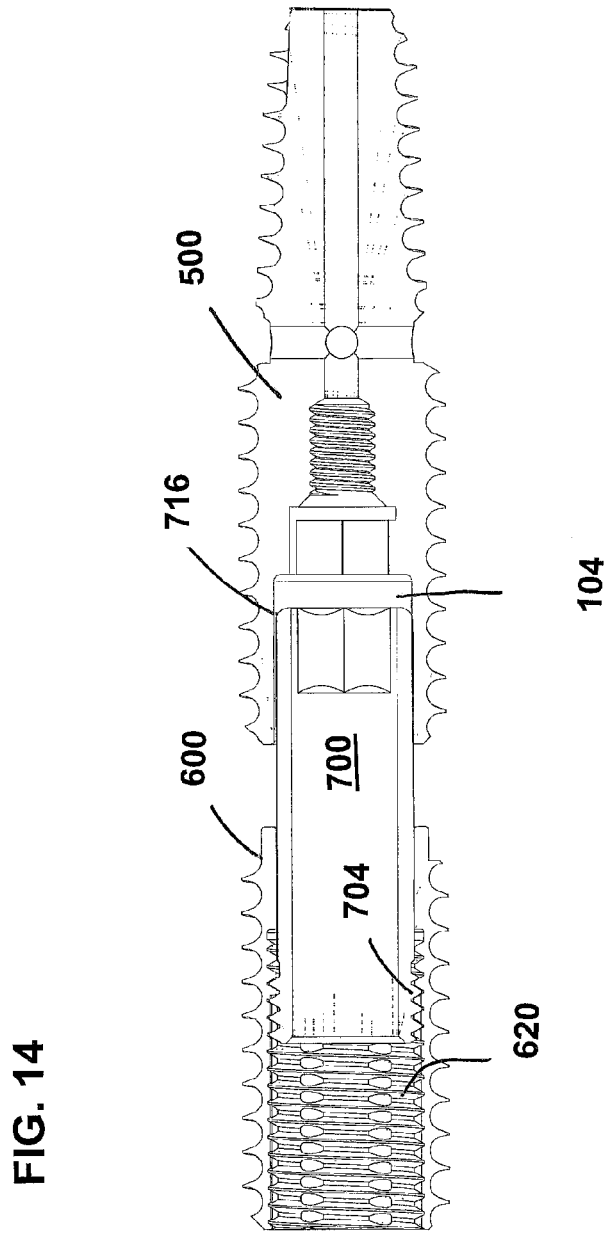
FIG. 14 shows the partial assembly of FIG. 13 after the spanning distraction rod has been retracted.

FIG. 14 shows the partial assembly of FIG. 13 after the spanning distraction rod 700 has been retracted such that the threaded portion 704 has moved in the proximal direction along internal threads 620 to introduce a gap 104 between the rounded distal end 716 of the spanning distraction rod 700 and the fusion rod 500.

Figure 15:
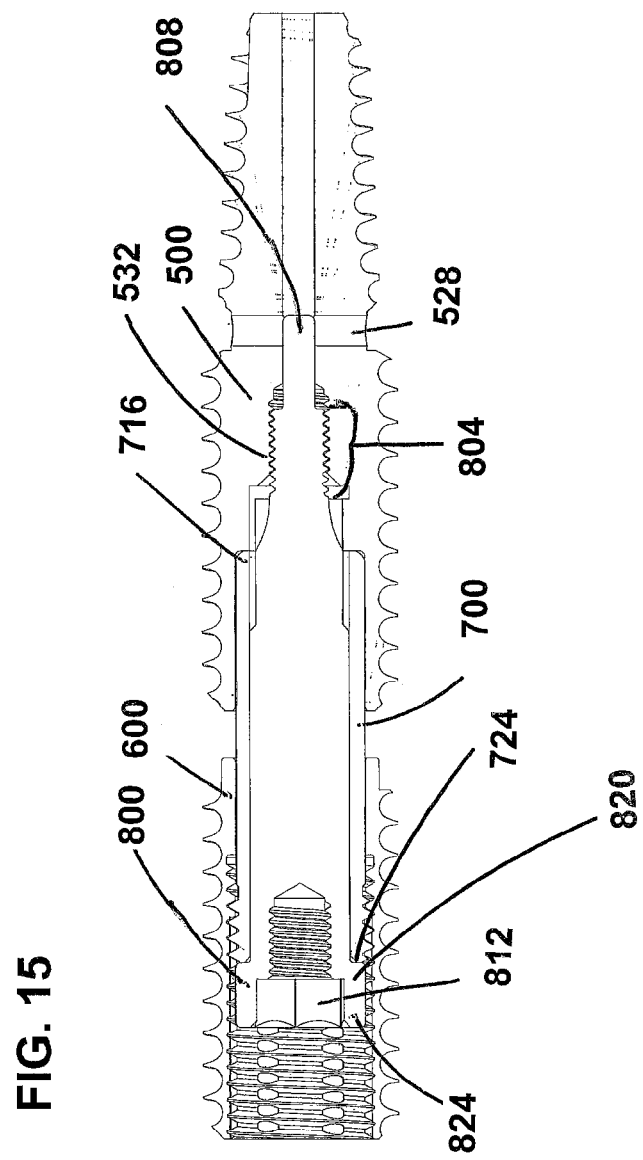
FIG. 15 shows the components from FIG. 13 after the insertion of fixation rod 800.

FIG. 15 shows the assembly after the insertion of fixation rod 800. An appropriate drive imparting torque to the driver engagement section 812 will cause the fixation rod 800 to spin relative to the proximal anchor 600 without moving in the proximal/distal direction. FIG. 15 shows the contact between shoulder 820 of the fixation rod 800 and the proximal end 724 of spanning distraction rod 700.

As the threaded section 804 engages the internal threaded section 532 of the fusion rod 500, the fusion rod 500 is pulled towards the proximal end 824 of the fixation rod 800 and the proximal anchor 600. With sufficient rotation of the fixation rod 800, the rounded distal end 716 of the spanning distraction rod 700 makes solid contact with the fusion rod 500. Now the minimum distance between the proximal anchor 600 and the fusion rod 500 is maintained by the spanning distraction rod 700 and the fixation rod 800 can be used to hold the distance between the proximal anchor 600 and the fusion rod 500 at no more than that minimum distance.

One of skill in the art will recognize that tightening the fixation rod 800 after the components have made contact will stretch the fixation rod 800 to put the fixation rod 800 in tension and help reduce any tendency to come loose by rotation. Excessive tightening may transfer torque to the thread bone interfaces or impart an unwanted rotation to the fusion rod.

Process of Implanting Assembly

Figure 16:
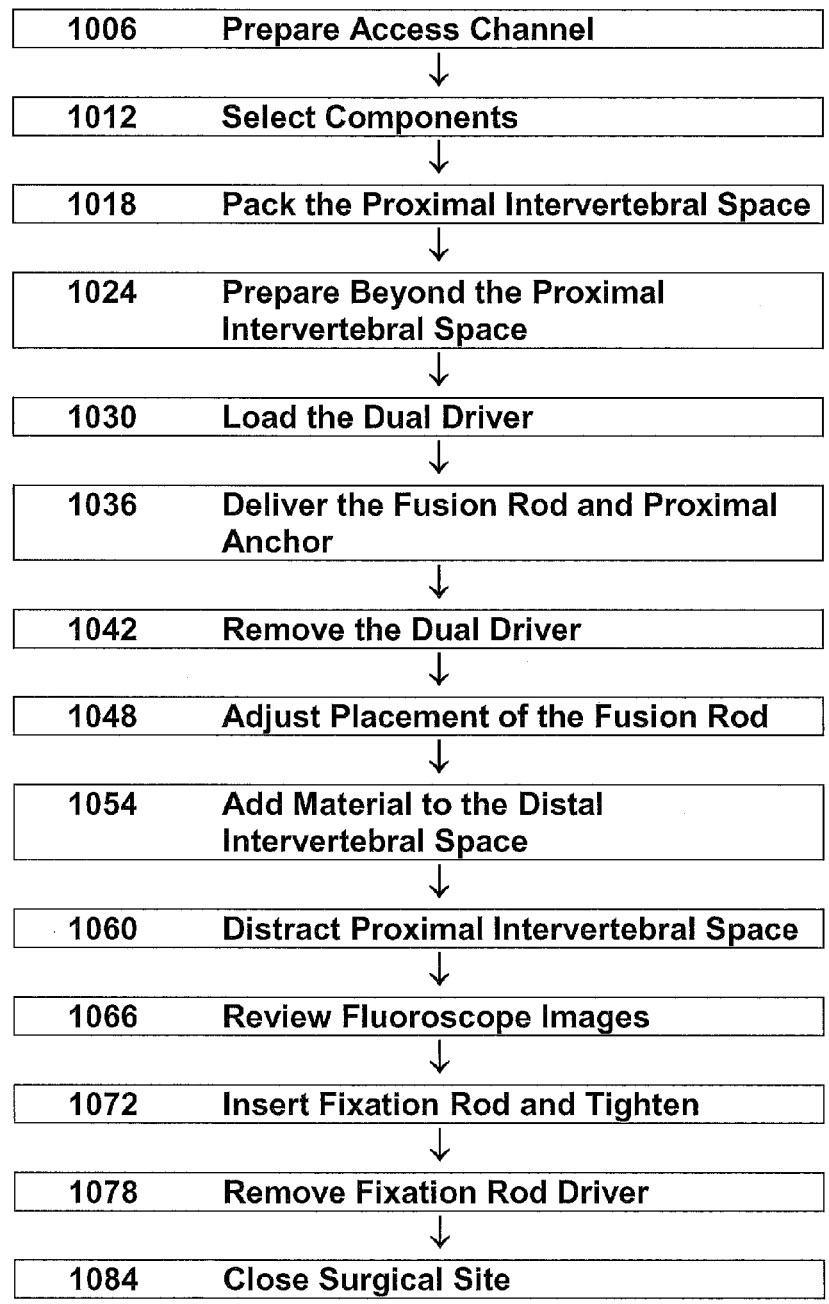
FIG. 16 is a flow chart for a process of implanting a two-level fusion assembly.

As the process of creating an access channel for use in a trans-sacral procedure has been covered in detail in a number of published patent applications and issued patents assigned to the assignee of this application, the process of creating a channel and preparing a set of vertebrae with bore holes of appropriate size for a given implant and thread will not be repeated here. The relevant information for the present disclosure with respect to two-level fusion assembly 100 may be summarized as set forth in FIG. 16 as process 1000.

1006—Prepare Access Channel A number of earlier applications with common assignee have addressed formation of a trans-sacral access channel 212 (FIG. 1). One of skill in the art will recognize that the specific bore sizes used for the access channel will be a function of the size components to be placed into the vertebral bodies and the desired difference between bore size and minor diameter of the threaded anchor to be placed in that vertebra. Examples of applications with material illustrating examples of access channel preparation may be found in U.S. Pat. No. 7,087,058 for Method and Apparatus for Providing Posterior or Anterior Trans-Sacral Access to Spinal Vertebrae and U.S. Patent Application Publication US-2007-0168036-A1 for Spinal Motion Preservation Assemblies (See FIG. 13). Both documents are incorporated by reference herein. One of skill in the art will recognize that the preparation of a disc space for fusion will be different than preparation for insertion of a motion preservation device as preparation for fusion may purposefully seek to cause bleeding of the vertebral endplates to promote fusion.

1012—Select Components. While the surgeon may have estimated the approximate size of the various components to be used in the two-level fusion assembly, the final selection amongst the available nominal sizes for components may be made during surgery given the feedback available to the surgeon from fluoroscopic imaging and from the opportunity to insert objects that serve as trials for inserting components of particular sizes.

1018—Pack the Proximal Intervertebral Space. After the disc material has been removed and the endplates have been prepared to promote fusion, the disc space may be filled with bone chips or other fusion promoting materials. Surgeons have used bone chips, including bone material removed from the patient during the creation of the bores through the vertebrae (autologous bone material) for this process. Some surgeons add other materials to the bone material to promote fusion. The particular choices used for packing the intervertebral space are beyond the scope of this disclosure but are known to those of skill in the art.

1024—Prepare Beyond the Proximal Intervertebral Space. Prepare the bore in the medial vertebral body 408. Prepare the distal intervertebral space 416 for fusion including packing with fusion promoting material such as bone chips. Prepare the bore in the distal vertebral body 404. The process of preparing the bores may include the insertion of objects that represent implants or provide markers to help in the selection of an implant of a particular size for the geometries of this particular surgery. This process may cause the surgeon to adjust the preliminary selections for implant sizes. Placing the trial objects in the bore may serve to dilate the bore.

1030—Load the Dual Driver. Thread the spanning distraction rod 700 into the proximal anchor 600 such that the spanning distraction rod 700 extends beyond the proximal anchor 600 a desired amount. The use of band 712 facilitates this process, although this band is not required. When loaded onto the driver with the fusion rod 500 and proximal anchor 600 engaged via keys with the driver and separated by a known distance (such as abutting), the proximal thread 508 of the fusion rod 500 and the external thread 604 of the proximal anchor 600 may be delivered by timed delivery so that the two threads of the same size are not cross threaded. As the maximum major diameter of the tapered thread on the distal thread 504 of fusion rod 500 is small enough to pass through the bores in the medial vertebral body 408 and the proximal vertebral body 412 without causing problems for the subsequent introduction of the larger threads, the delivery of distal thread 504 does not need to be done by timed delivery. As described in earlier applications and patents, the use of a distal thread that has a smaller major diameter than the proximal thread allows for distraction through use of dissimilar thread pitch.

A retention rod within the driver (not shown) may be engaged with the interior threaded section 532 of the fusion rod 500 to pull the fusion rod 500 tight onto the driver and against the proximal anchor 600.

1036—Deliver the Fusion Rod and Proximal Anchor. The spanning distraction rod 700 is on the driver and between the fusion rod 500 and proximal anchor 600. The driver and components may be loaded over a guide wire. The driver may threadedly advance the components until the proximal anchor 600 is positioned appropriately with respect to the proximal vertebral body 412. The positioning of the proximal anchor 600 relative to the sacrum (if the sacrum is the proximal vertebral body 412) may call for a portion of the external thread 604 to protrude slightly on both the proximal and distal ends of the bore in the sacrum.

1042—Remove the Dual Driver. If a retention rod was engaged with the interior threaded section 532, this engagement will be unthreaded before removal of the dual driver.

1048—Adjust Placement of the Fusion Rod. If desired, use a driver that will pass through the interior of the spanning distraction rod 700 to engage the fusion rod 500 but not the proximal anchor 600. In order to minimize damage to the thread/bone interface, it may be preferred to avoid moving the fusion rod 500 proximally.

1054—Add Material to the Distal Intervertebral Space. Optionally, additional material may be added to the previously packed distal intervertebral space 420 through the set of ports 528 in the fusion rod 500.

1060—Distract Proximal Intervertebral Space. Engage the set of notches 624 with a counter torque tube or other device to preclude unintended rotation of the proximal anchor 600. Insert driver through the counter torque tube to engage the spanning distraction rod 700 and advance the spanning distraction rod 700 to allow the rounded distal end 716 of the spanning distraction rod 700 to push against the anchored fusion rod 500 to increase the distance between the medial vertebral body 408 and the proximal vertebral body 412. This process may be characterized as a means for distracting, that is increasing the distraction of the intervertebral space by increasing the distance between the anchors.

One of skill in the art will appreciate that the counter torque tube could engage some other feature on the proximal end 612 of the proximal anchor 600 instead of the set of notches 624, including protuberances (this alternative is not shown) that extend proximally from the proximal end of the proximal anchor. The set of notches 624 or another feature accessible on the proximal face of the proximal anchor serves as a means for engaging the proximal end of the proximal anchor.

1066—Review Fluoroscope Images. If the amount of distraction imposed by the spanning distraction rod 700 is too much, then retract the spanning distraction rod 700 to leave a small gap 104 (FIG. 14) between the rounded distal end 716 and the fusion rod 500. The gap 104 will not be visible in fluoroscopic images as it will be internal to the fusion rod 500. However, the distance will be known (less any shifting of the vertebrae) as a function of the thread pitch and the number of turns that the spanning distraction rod 700 is retracted. The ability of the fixation rod 800 to eliminate a hyper-distraction gap is limited by the length of the threaded section with the external thread 804. In other words, the gap (FIG. 14 element 104) cannot be so wide that the fixation rod 800 is unable to engage the internal threaded section 532 of the fusion rod 500. The same would be true if the surgeon desired to reduce the pre-surgery disc space height.

One of skill in the art will appreciate that extending the linear distances for the external thread 804 and threaded section 532 increase the ability to decrease intervertebral disc space height.

1072—Insert Fixation Rod and Tighten. The fixation rod 800 may be retained on the driver by a retention rod that engages the internal threaded bore 816. The external thread 804 engages the internal threaded section 532 of the fusion rod 500. Optionally, the length of the fixation rod may be set to extend up to the set of ports 528 in the fusion rod to prevent ingress of material from the distal intervertebral space 420 (FIG. 1) through the ports 528 into the fusion rod 500.

As shown in FIG. 15, the fixation rod 800 for use in a particular combination of components may be designed so that the distal end 808 of the fixation rod 800 fills the fluoroscopic image of the ports 528 when the fixation rod 800 is fully inserted. This combination of component geometries allows the surgeon to confirm position of the fixation rod 800 using fluoroscopy. Thus, the assembly has a means for confirming the position for the fixation rod tip.

The insertion of the fixation rod 800 will remove the gap 104 introduced by inadvertent hyper-distraction of the proximal intervertebral disc space 420 (FIG. 1). This process may be characterized as a means for retracting, that is reducing the amount of distraction in an intervertebral space by reducing the distance between anchors.

The fixation rod 800 may be tightened a prescribed amount such as finger tight or to another set amount of torque based upon a balance against wishing to tighten the two-level fusion assembly 100 and a desire not to cause unwanted consequences to the engagements of threads with the vertebral bodies.

1078—Remove Fixation Rod Driver. This may include unthreading a retention rod.

1084—Close Surgical Site. This step may include removal of a guide wire and a cannula docked to the sacrum in addition to closing the surgical access path.

Process to Set Distraction Distance

Figure 17:
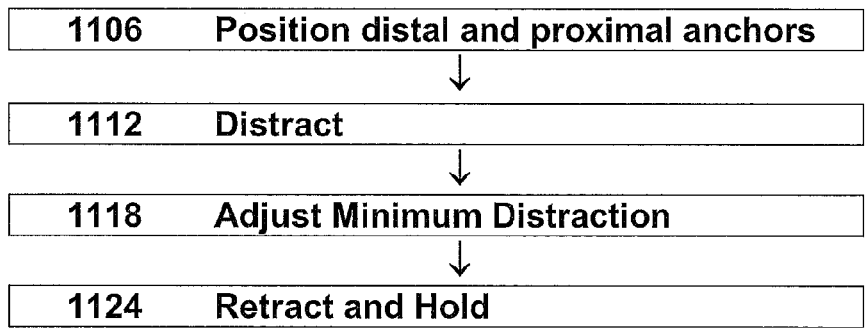
FIG. 17 is a process to set distraction distance.

FIG. 17 highlights the process 1100 to set the distraction in the proximal intervertebral space 420.

1106—Position Distal and Proximal Anchors. The fusion rod 500 and the proximal anchor 600 serve as the distal and proximal anchors across the proximal intervertebral space 420.

1112—Distract. The spanning distraction rod 700 may be threadedly advanced relative to the proximal anchor 600 to push upon the distal anchor (in this case fusion rod 500) to increase the minimum distance between the two anchors and thus increase the distance between the adjacent vertebral bodies threadedly engaged with the two anchors.

1118—Adjust Minimum Distraction. Based upon review of fluoroscope images or other surgical reasons, reduce the minimum distraction imposed by the spanning distraction rod 700 by reversing a portion of the threaded advance of the spanning distraction rod 700 relative to the proximal anchor 600. Not every surgical procedure will include an adjustment of the minimum distraction but the availability of this step facilitates the surgical process as the surgeon can dial in the optimal distraction by trying a range of distractions and viewing the results in fluoroscopic images.

1124—Retract and Hold. The addition of the fixation rod 800 that pulls the two anchors together allows the retraction (reduction of distraction) if needed and pulls the assembly together. The distance between the two anchors is now held by the combination of pushing and pulling.

Three Anchor Solution

Figure 18:
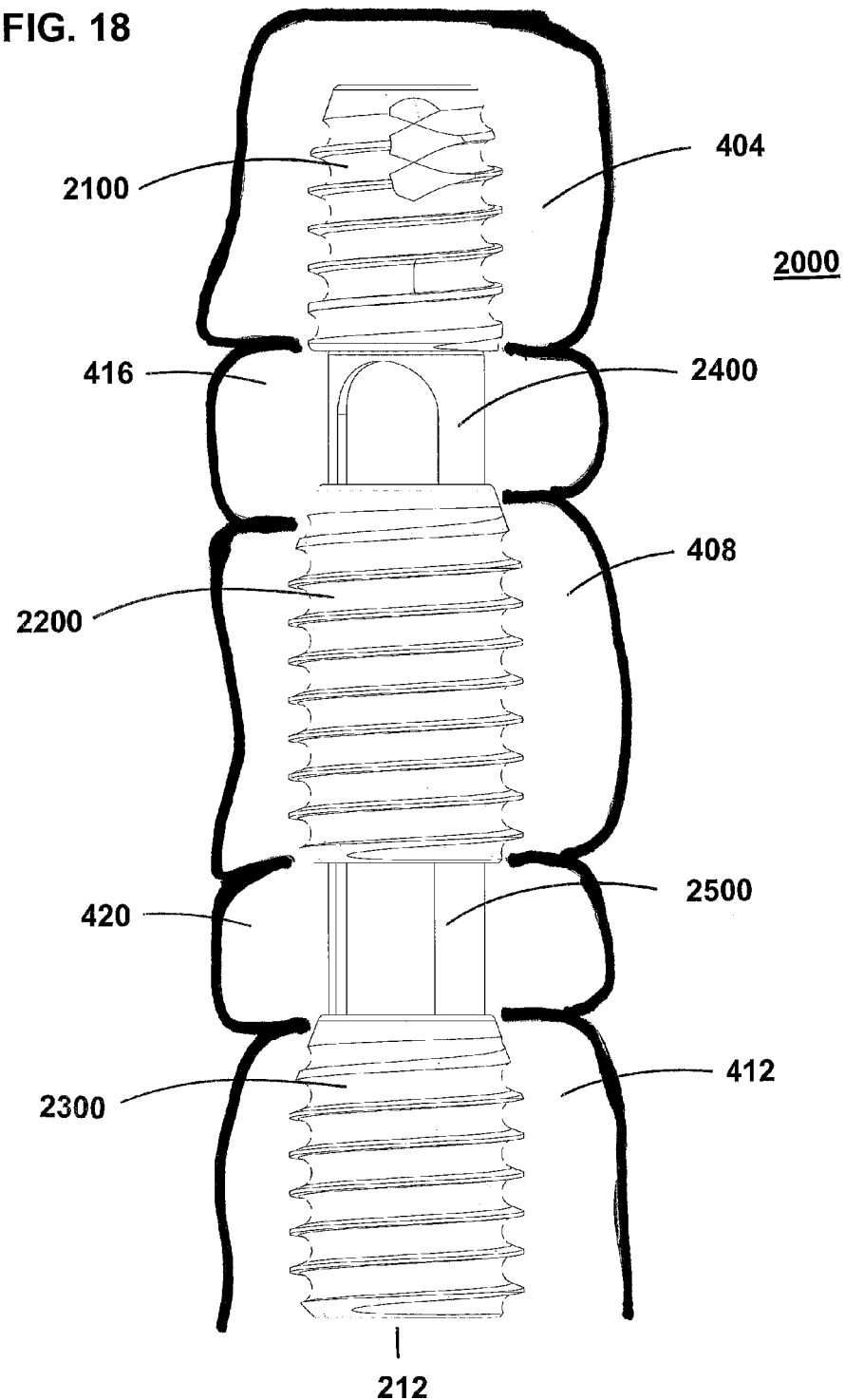
FIG. 18 shows a lateral view of a two-level fusion assembly engaged with three adjacent vertebrae.

A second two-level fusion assembly 2000 is shown in a lateral view of a portion of a human spine placed in three adjacent vertebrae in FIG. 18. FIG. 18 is not a cross section but rather a view of the spinal implant visible within the spine somewhat like a fluoroscope image. As with FIG. 1, FIG. 18 omits biological structures of the spine not relevant to the present disclosure. As with FIG. 1, a portion of a spine is represented by distal vertebral body 404, medial vertebral body 408, proximal vertebral body 412, distal intervertebral space 416, and proximal intervertebral space 420.

Visible in FIG. 18 are the three anchors: distal anchor 2100, medial anchor 2200, and proximal anchor 2300. Partially visible in FIG. 18 are the distal spanning distraction rod 2400 and the proximal spanning distraction rod 2500. As will become evident upon study of subsequent figures, partially visible though the large ports (discussed below) but not recognizable are the distal fixation rod and the proximal fixation rod.

Figure 19:
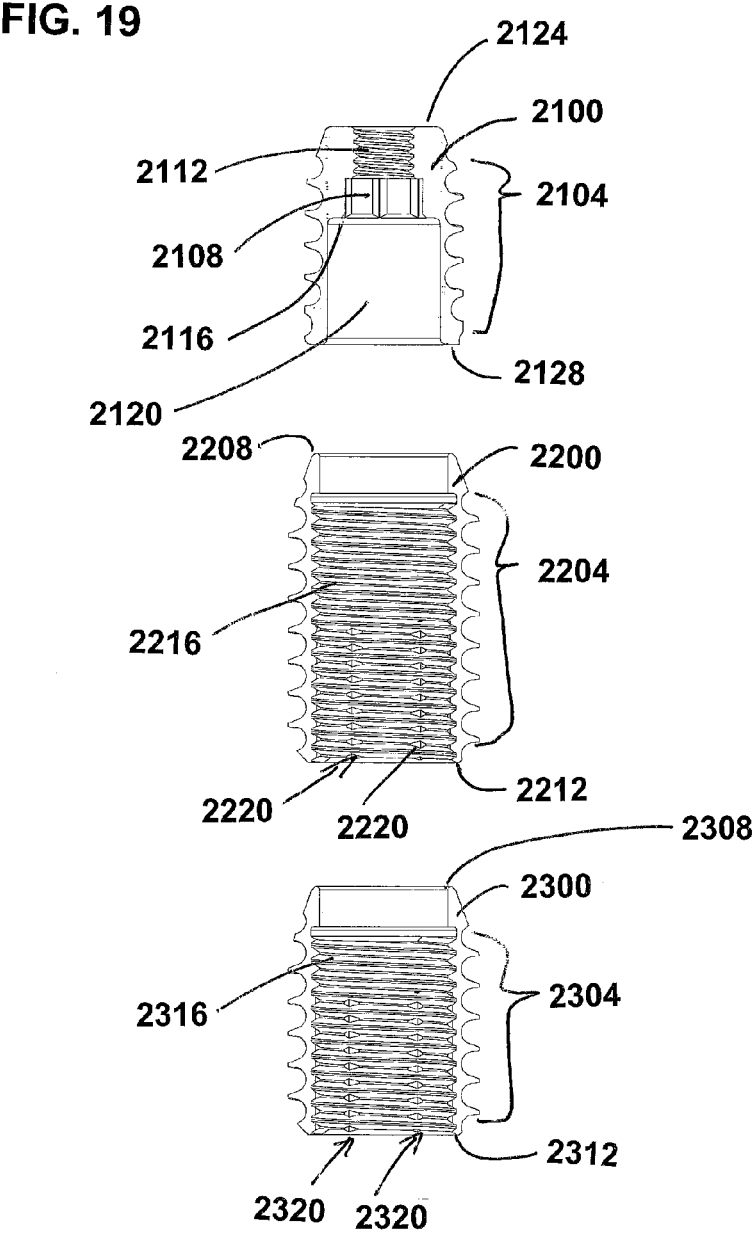
FIG. 19 provides cross sections of the three anchors show in FIG. 18.

FIG. 19 provides cross sections of the three anchors. The distal anchor 2100 has an external thread 2104, a driver engagement section 2108, and a threaded bore 2112 which may be used with a retention rod to hold the distal anchor 2100 to a driver. A shoulder 2116 is at the distal end of a cylindrical cavity 2120 that is open at the proximal end 2128 of the distal anchor 2100. The distal anchor 2100 may be placed over a guide wire as it is open from the proximal end 2128 to the distal end 2124.

The medial anchor 2200 has an exterior thread 2204. The interior of the medial anchor 2200 is open from the distal end 2208 to the proximal end 2212. The interior has a threaded section 2216 with sets of notches 2220 that may be engaged by a driver.

The proximal anchor 2300 has an external thread 2304 and is open in the interior from the distal end 2308 to the proximal end 2312. The interior has a threaded section 2316 with sets of notches 2320 that may be engaged by a driver. Medial anchor 2200 and proximal anchor 2300 may use the same major diameter and thread pitch such that the proximal anchor may be delivered via timed delivery to engage into a thread path previously cut by the medial anchor 2200 as the medial anchor 2200 was advanced through the proximal vertebral body 412 (FIG. 18).

Medial anchor 2200 and proximal anchor 2300 differ principally in length. A system of components could be implemented so that a surgeon may pick appropriate anchors from a set of anchors of different lengths to become the medial and proximal anchors for a given procedure. Thus a particular size of anchor used as a medial anchor for one patient may be used as a proximal anchor for a different patient.

Figure 20:
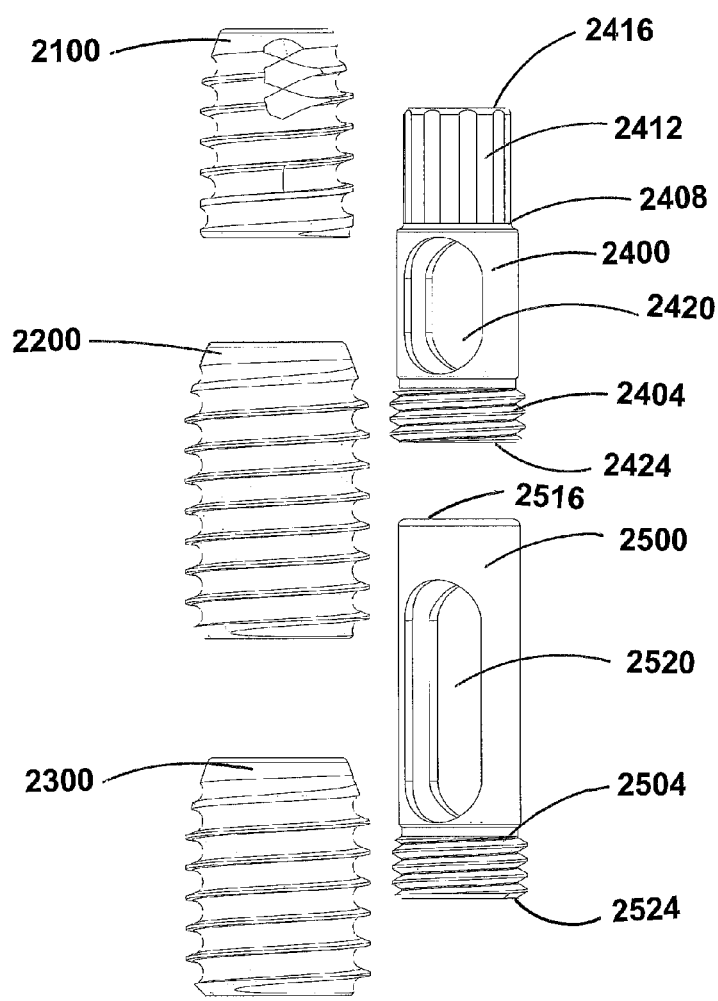
FIG. 20 the distal spanning distraction rod, the proximal spanning distraction rod, and the three anchors from FIG. 18.

FIG. 20 shows the three anchors (2100, 2200, and 2300). FIG. 20 also shows the distal spanning distraction rod 2400 and the proximal spanning distraction rod 2500.

Distal spanning distraction rod 2400 has an external thread 2404, shoulder 2408, and fluted section 2412. The distal spanning distraction rod 2400 has an interior channel (shown below) from the proximal end 2424 to the distal end 2416. Distal spanning distraction rod 2400 also has a set of large ports 2420.

Proximal spanning distraction rod 2500 has an external thread 2504. The proximal spanning distraction rod 2500 has an interior channel (shown below) from the proximal end 2524 to the distal end 2516. Proximal spanning distraction rod 2500 also has a set of large ports 2520.

These large ports (2420 and 2520) may be used with an appropriate tool to deliver fusion promoting material (such as bone chips) to the intervertebral disc space. The process of delivering fusion promoting material may include rotating the spanning distraction rod ninety degrees to allow the ports to face a greater range of directions in the intervertebral disc space.

One of skill in the art will recognize that a single port may be used on a spanning distraction rod along with perhaps a greater need to rotate the single port to deliver the material. Alternatively three or more ports could be used instead of two ports as shown here.

Fixed Distraction of Distal Space

Figure 21:
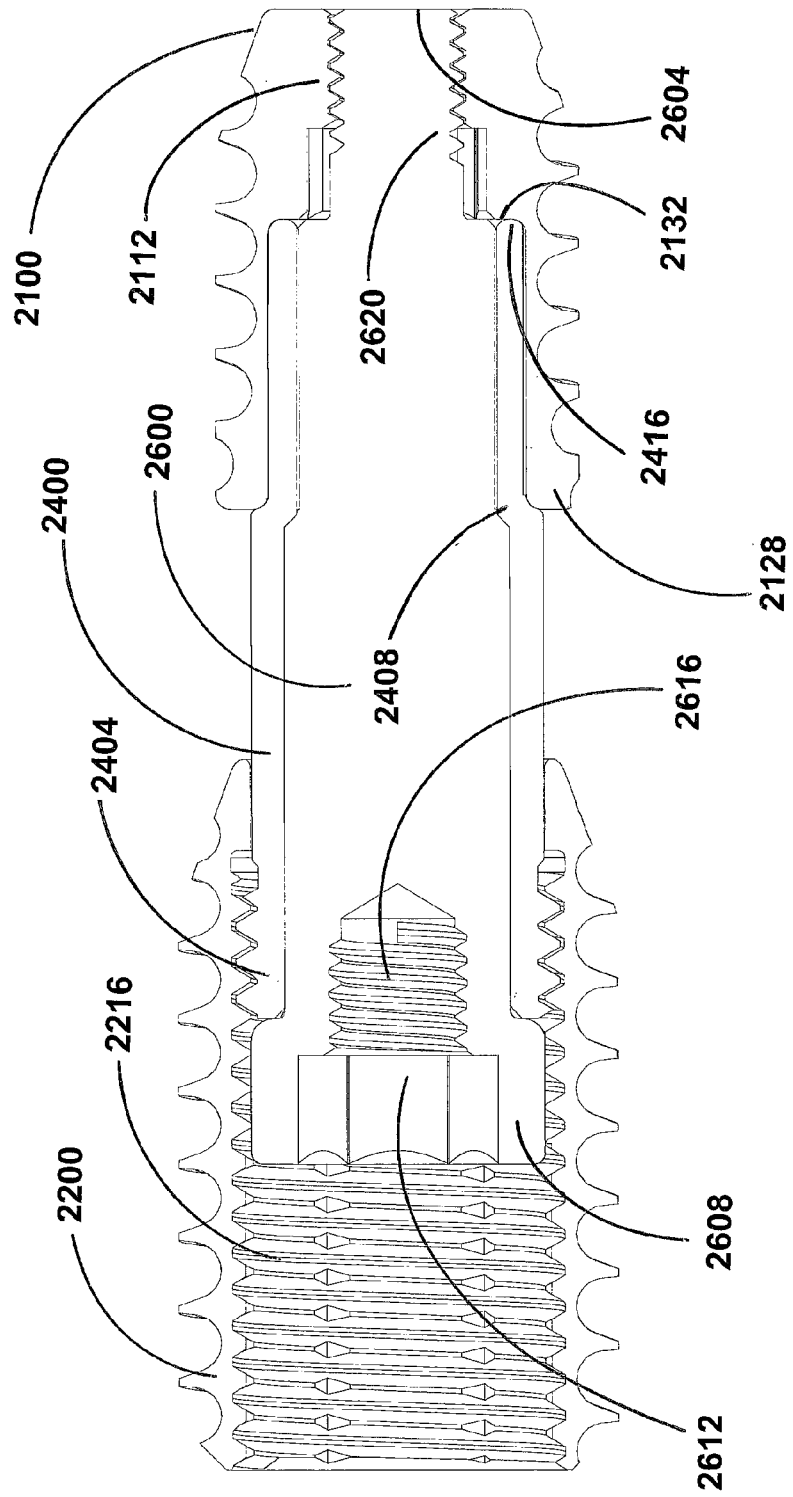
FIG. 21 illustrates the completed subassembly after insertion of the distal fixation rod.

FIG. 21 illustrates the completed subassembly after insertion of the distal fixation rod 2600 after delivery of material to the distal intervertebral disc space through the large ports (2420 in FIG. 20). An option open to surgeons, is to purposefully hyper-distract the distal intervertebral disc space (416 in FIG. 18) to facilitate the delivery of material into the oversized gap between the distal vertebral body (404 in FIG. 18) and the medial vertebral body (408 in FIG. 18).

One of skill in the art will appreciate that one could use the large ports 2420 to deliver devices to the intervertebral disc space including small fusion cages, spherical cages, expandable cages, balloons, and other devices that would assist in the process of creating a stable fused space. Likewise, one could deliver devices to the intervertebral disc space including small fusion cages, spherical cages, expandable cages, balloons, and other devices to the hyper-distracted disc space through any of the non-trans-sacral surgical approaches known in the art of spinal surgery.

One of skill in the art will appreciate that after the disc space is distracted or hyper-distracted there are options to introduce tools of various types into the disc space that may not have fit within an unusually thin disc space. Thus, after distraction or hyper-distraction, one could use the large ports 2420 to provide access to the intervertebral disc space for introduction of the distal end of tools such as: surgical instruments to further prepare the disc space, visualization instruments, or other tools that would assist in the process of providing therapy. Likewise, after distraction or hyper-distraction, one could introduce: surgical instruments to further prepare the disc space, visualization instruments, or other tools that would assist in the process of providing therapy space through any of the non-trans-sacral surgical approaches known in the art of spinal surgery.

Figure 22:
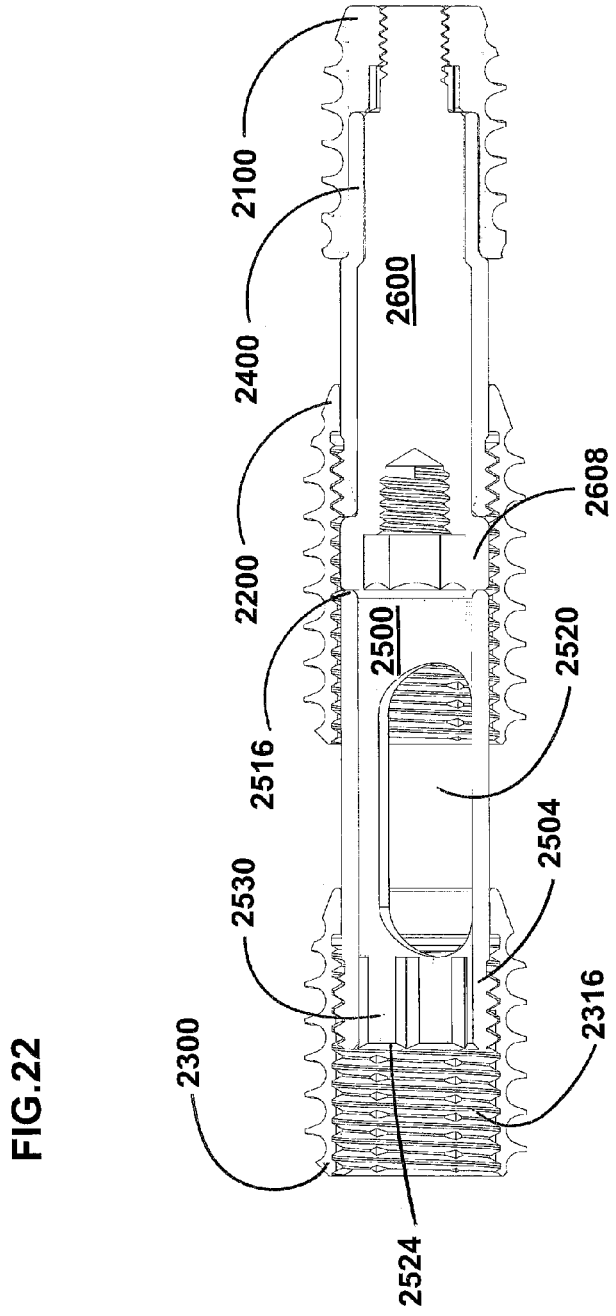
FIG. 22 shows the addition of proximal spanning distraction rod to the sub-assembly of FIG. 21.

After filling, the distal spanning distraction rod 2400 could be rotated by a driver interacting with the driver engagement section of the distal spanning distraction rod 2400 located in the proximal end of the spanning distraction rod 2400 analogous to the driver engagement section for proximal spanning distraction rod 2500 (see element 2530 in FIG. 22). Referencing FIG. 21, rotation in the appropriate direction based on the thread handedness would move the external thread 2404 relative to the threaded section 2216 of medial anchor 2200 to back off the hyper-distraction by a predictable distance based on number of turns and thread pitch.

Distal Fixation Rod

The distal fixation rod 2600 is visible in FIG. 21. The distal fixation rod 2600 has: a distal end 2604, a proximal end 2608, a driver engagement section 2612, a threaded bore 2616 for use with a retention rod, and a threaded section 2620 near the distal end 2604.

Insertion and rotation of the distal fixation rod 2600 engages the threaded section 2620 with the threaded bore 2112 of the distal anchor 2100. When tightened, the distal fixation rod 2600 will pull the two anchors (2100 and 2200) together to the minimum distraction distance set by the position of the distal spanning distraction rod 2400 within the medial anchor 2200.

By choice of component lengths a designer may choose to have the proximal end 2128 of the distal anchor 2100 rest firmly against the shoulder 2408 of the distal spanning distraction rod 2400. Alternatively, the distal end 2416 of the distal spanning distraction rod 2400 will rest against shoulder 2132 of the distal anchor 2100.

The movement of the endplates of the two vertebral bodies (404 and 408) anchored to the two anchors (2100 and 2200) will compress material used to fully fill a hyper-distracted distal intervertebral disc space 416. Compression may promote fusion by either accelerating the process or increasing the likelihood of successful fusion.

One theory supporting the use of compression is Wolff's law which suggests that bone forming cells, osteoblasts, require loading in order to promote growth.

Whether or not the use of the distal fixation rod 2600 removes intentional hyper-distraction added to allow compression of inserted material, or removes unintended hyper-distraction from a process of testing various distraction amounts via fluoroscopy as discussed above, the use of the distal fixation rod 2600 will lock that portion of the assembly so that the distance between the two anchors (2100 and 2200) is fixed.

Fixation of the distance between the anchors may be advantageous when a patient is undergoing several different procedures during one surgical session and must be repositioned. Repositioning a substantially lateral patient (without gravity to press the vertebrae downward) could potentially change the distance between adjacent vertebrae unless prevented by the presence of the fixation rod. Fixation may serve other patients in other ways.

Another advantage of fixation is that may provide an extra layer of protection to eliminate any slight risk of the proximal anchor migrating away from the rest of the assembly Adding Distraction to the Proximal Motion Segment After fixation of the distraction in the distal intervertebral section, the proximal intervertebral disc space (420 in FIG. 18) may be addressed. FIG. 22 shows the addition of proximal spanning distraction rod 2500 to the sub-assembly of FIG. 21. Proximal spanning distraction rod 2500 has a driver engagement section 2530 at the proximal end 2524.

Rotation of the proximal spanning distraction rod 2500 through use of a driver engaged with the driver engagement section 2530 will advance the external thread 2504 relative to the threaded section 2316 of the proximal anchor 2300. Advancing the proximal spanning distraction rod 2500 will cause the distal end 2516 of the proximal spanning rod 2500 to push against the proximal end 2608 of the distal fixation rod 2600 to push the sub-assembly including the medial anchor 2200 and the distal anchor 2100 away from the proximal anchor 2300.

As discussed above in connection with the use of distal spanning distraction rod 2400, the large ports 2520 may be used to deliver material to the proximal intervertebral disc space (420 in FIG. 18), including the rotation of the ports by ninety degrees to facilitate delivery to all portions of the intervertebral disc space.

As discussed above there may be inadvertent hyper-distraction as the surgeon seeks to dial in the optimal spacing between anchors and tests a proposed position of the proximal spanning distraction rod 2500 that provides too much distraction based upon an evaluation of the positioning via fluoroscopy. As mentioned above, the proximal intervertebral disc space may be intentionally hyper-distracted in order to allow overfilling of the oversized proximal intervertebral disc space (420 in FIG. 18) so that the filling material may be compressed.

Proximal Fixation Rod

Figure 23:
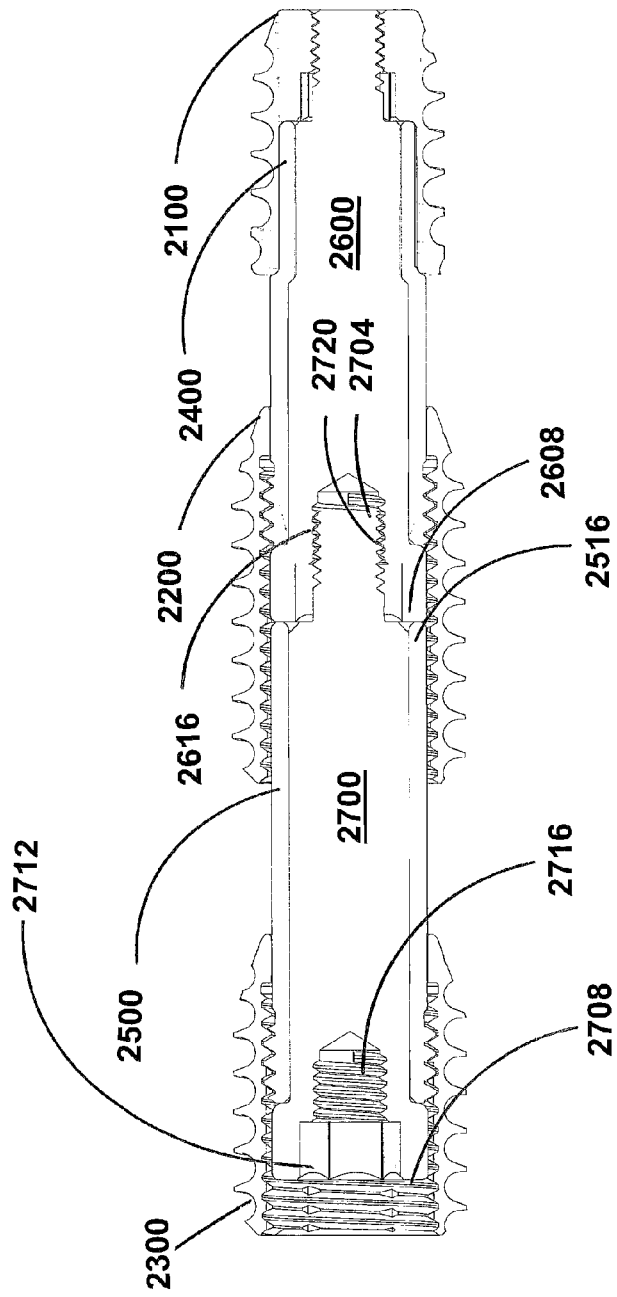
FIG. 23 shows the addition of the proximal fixation rod to the sub-assembly of FIG. 21.

The proximal fixation rod 2700 is visible in FIG. 23. The proximal fixation rod 2700 has: a distal end 2704, a proximal end 2708, a driver engagement section 2712, a threaded bore 2716 for use with a retention rod, and a threaded section 2720 near the distal end 2704.

Insertion of the proximal fixation rod 2700 engages the threaded section 2720 with the threaded bore 2616 of the distal fixation rod 2600. When tightened, the proximal fixation rod 2700 will decrease the distance between the proximal anchor 2300 and the other two anchors (2100 and 2200) to the minimum distraction distance set by the position of the proximal spanning distraction rod 2500 within the proximal anchor 2300.

The proximal end 2608 of the distal fixation rod 2600 will rest firmly against the distal end 2516 of the proximal spanning distraction rod 2500.

If the intervertebral disc space was hyper-distracted and fully filled, the movement of the endplates of the two vertebral bodies (408 and 412) anchored to the two anchors (2200 and 2300) will compress material used to fully fill the hyper-distracted proximal intervertebral disc space 420.

Method of Overfilling and Compressing Material

Figure 24:
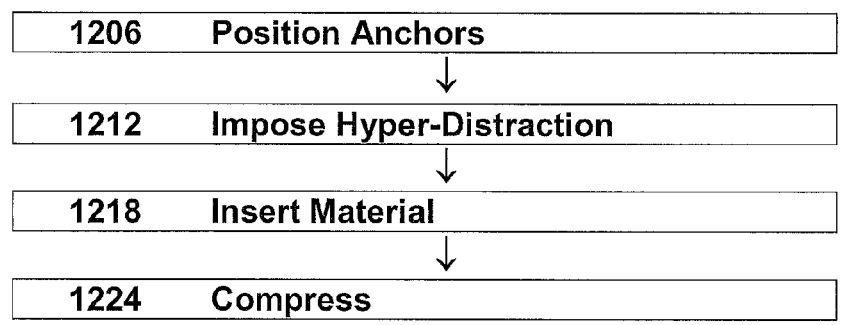
FIG. 24 is a flow chart for the process of compressing inserted material within an intervertebral disc space.

FIG. 24 provides a short flow chart to summarize the process 1200 of compressing inserted material within an intervertebral disc space.

1206—Position Anchors. Position a pair of anchors into the two adjacent vertebrae on either side of an intervertebral disc space.

1212—Impose Hyper-Distraction. By hyper-distraction it is meant that the minimum distance between anchors is temporarily set at a larger value than desired in the final assembly.

1218—Insert Material. Insert material into the intervertebral disc space. As the anchors are connected to the two vertebrae and the two anchors are positioned in a hyper-distracted distance apart from one another, the intervertebral disc space has a larger distance between vertebrae than desired in the final assembly. Filling this disc space full of material makes compression possible. The material may include bone chips and material to promote bone growth. The material may include various devices that may help promote stability or structural support. Thus, the material may include fusion cages or other man-made devices.

The inserted material may come from a trans-sacral route or through a non-trans-sacral route.

1224—Compress. Use of a fixation rod pulls the anchors towards one another and thus pulls the two vertebrae towards one another to reduce the space between the vertebrae. The compression of material placed in the intervertebral disc space may promote the fusion process by increasing contact, collapsing any voids in the inserted material, encouraging bone growth by the imposition of the compressive stress, and providing other benefits.

Use of Single Fixation Rod for Three Anchors

Figure 25:
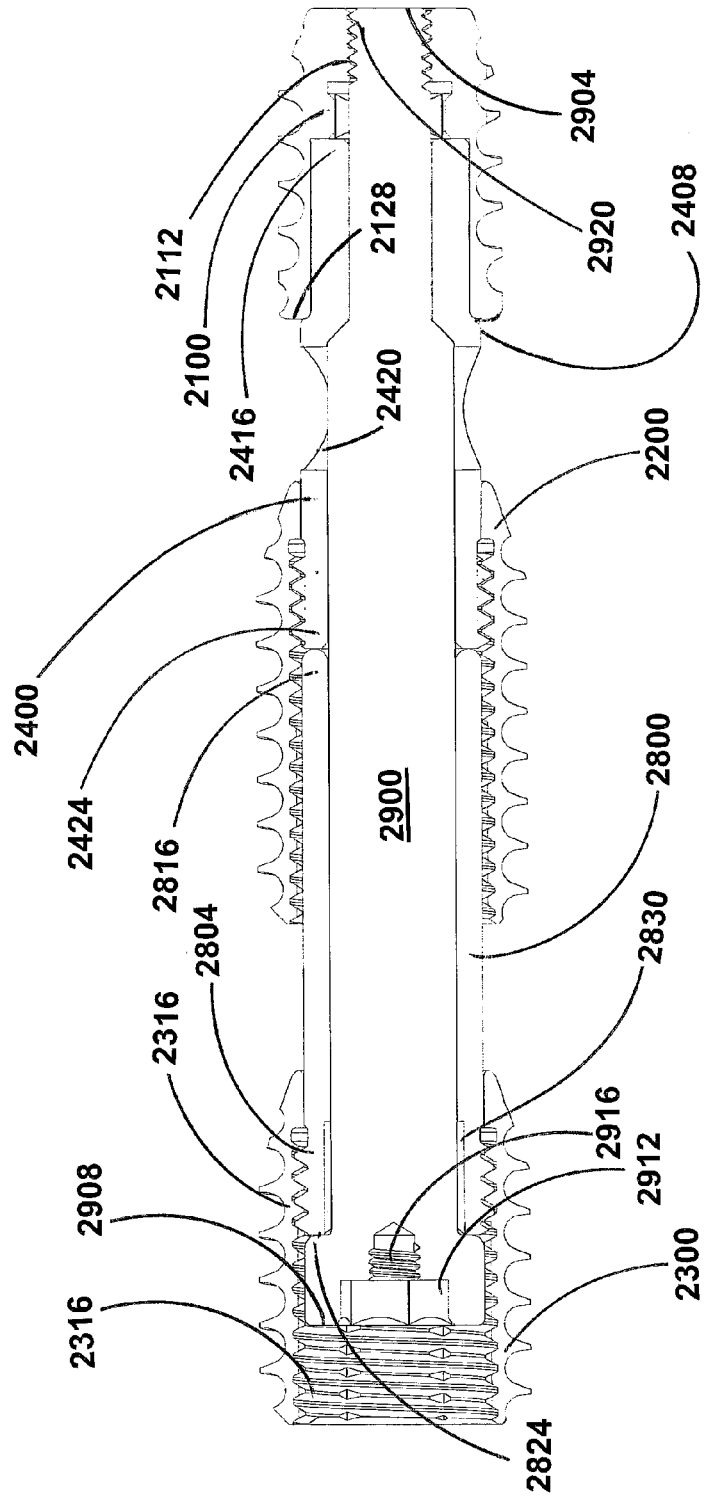
FIG. 25 is a cross section view of an assembly using a single fixation rod.

FIG. 25 has a different configuration with single fixation rod 2900 that connects the distal anchor 2100 to the proximal anchor 2300. As this configuration has some commonalities with the configurations discussed above, this description will be brief.

The minimum distance between distal anchor 2100 and medial anchor 2200 may be set through use of distal spanning distraction rod 2400 through contact by the distal end 2416 with the interior of the distal anchor 2100 or by contact between the shoulder 2408 with the proximal end 2128 of the distal anchor 2100 (or by a combination of both contacts). Most likely, through just the contact provided by the distal end 2416 by adjusting dimensions so that the distal end 2416 makes contact first.

The minimum distance between the medial anchor 2200 and the distal anchor 2100 may be controlled by rotating the distal spanning distraction rod with a driver that interacts with a driver engagement section (hidden in this cross section by 2900) in the proximal end 2424 of the distal spanning distraction rod 2400 to threadedly advance the distal spanning distraction rod 2400 relative to the medial anchor 2200. As described above, the large ports 2420 (visible here based on the cross section taken) may be used to deliver material to the distal intervertebral disc space (416 of FIG. 18). The spanning distraction rod 2400 may have a fluted section as discussed above.

Long Proximal Spanning Distraction Rod

Continuing to refer to FIG. 25, long proximal spanning distraction rod 2800 may be used to impose a minimum distance between the proximal anchor 2300 and the medial anchor 2200 through threaded advancement of the external thread 2804 of the long proximal spanning distraction rod 2800 and the threaded section 2316 of the proximal anchor 2300. Threaded advancement is controlled by the use of an appropriate driver to engage a driver engagement section 2830 in the proximal end 2824 of the long proximal spanning distraction rod. Threaded advancement of the long proximal spanning distraction rod 2800 causes contact and pushing between the distal end 2816 and the proximal end 2424 of the distal spanning distraction rod 2400.

The long proximal spanning distraction rod 2800 may have large ports (not visible in this cross section) which may be used to deliver material to the proximal intervertebral disc space (420 in FIG. 18).

Single Fixation Rod

FIG. 25 shows the assembly after insertion of the single fixation rod 2900. Single fixation rod 2900 has an external thread 2920 at the distal end 2904 that engages with the threaded bore 2112 of the distal anchor 2100. Single fixation rod 2900 may be rotated through use of a driver that engages a driver engagement section 2912 at the proximal end 2908 and optionally engages a threaded bore 2916 with a retention rod.

The use of a single fixation rod 2900 does not provide the flexibility afforded by the use of two fixation rods and thus is not as well adapted to provide compression of material provided to each of the two intervertebral disc spaces. The single fixation rod 2900 may remove small amounts of hyper-distraction induced by processes that rotate the large ports to provide improved access to the disc space while using the large ports to deliver material to the disc space.

One Level Assembly

Figure 26:
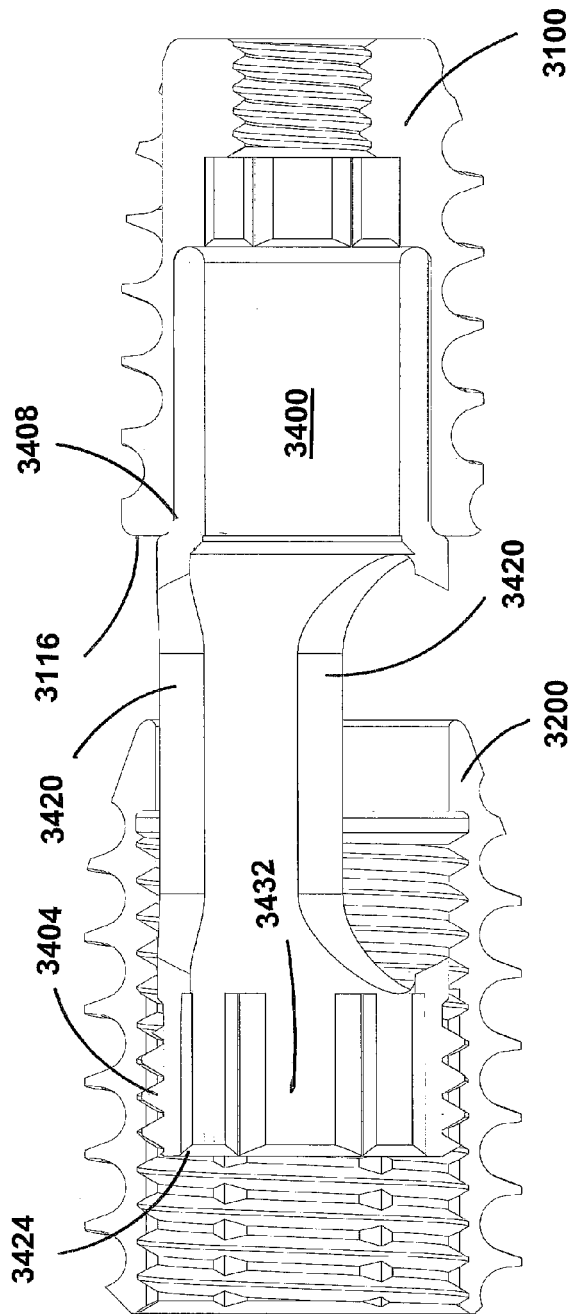
FIG. 26 is a cross section of a sub-assembly before the addition of the fixation rod.
Figure 27:
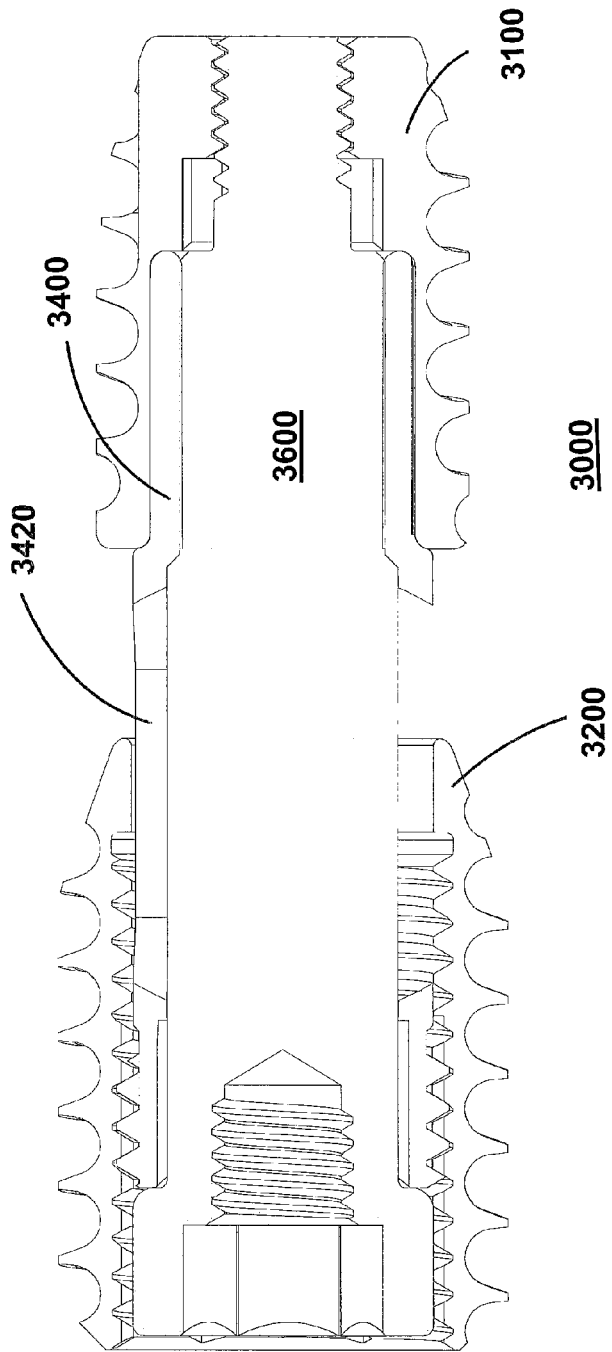
FIG. 27 is the cross section of FIG. 26 after the addition of the fixation rod.

FIG. 26 and FIG. 27 show assembly 3000 with a distal anchor 3100, proximal anchor 3200 spanning distraction rod 3400, and fixation rod 3600. FIG. 26 shows the partial assembly before the addition of the fixation rod 3600. FIG. 27 shows the completed assembly 3000 after the addition of the fixation rod 3600.

The one level assembly shown in FIG. 26 and FIG. 27 has some similarities to FIG. 21 that showed a partial assembly of a two-level modular assembly. More specifically, FIG. 21 showed the components associated with setting the intervertebral distance for the distal intervertebral space. The major components in FIG. 21 are the distal anchor 2100, medial anchor 2200, distal spanning distraction rod 2400, and distal fixation rod 2600.

Details present in FIG. 26 include the external thread 3404 near the proximal end 3424 of the spanning distraction rod 3400, driver engagement section 3432, portions of the large ports 3420, shoulder 3408 which may be designed to contact proximal end 3116 of distal anchor 3100.

As with examples discussed above, the combination of the spanning distraction rod 3400 and fixation rod 3600 sets the distance between the distal anchor 3100 and proximal anchor 3200.

Frequently, a single level therapy will be applied to the L5/S1 motion segment. In contrast, the distal motion segment for a multi-level therapy cannot be the L5/S1 motion segment if the approach route is a trans-sacral route as L5/S1 is the most proximal motion segment. Thus, one difference that appears in the example shown in FIG. 26 and FIG. 27 versus what is shown in FIG. 21 is that the anchors are sized for placement in S1 and L5 rather than L5 and L4.

A second difference is that the spanning distraction rod 3400 occupies a greater percentage of the interior of proximal anchor 3200 than does the distal spanning distraction rod 2400 with respect to the medial anchor 2200. Likewise the fixation rod 3600 occupies a substantial portion of the interior of proximal anchor 3200. As proximal anchor 3200 is not a medial anchor involved with two motion segments, there is no need for the proximal anchor 3200 to have space to receive a proximal spanning distraction rod or a proximal fixation rod.

Use of Dissimilar Thread Pitch

An alternative to using a spanning distraction rod that is threaded on the proximal end only and used to push the distal anchor, is a spanning distraction rod that is threaded on both the proximal and distal ends and uses dissimilar thread pitch to provide a controlled distraction. The concept of dissimilar thread pitch was discussed above in connection with the use on a distraction rod.

Figure 28:
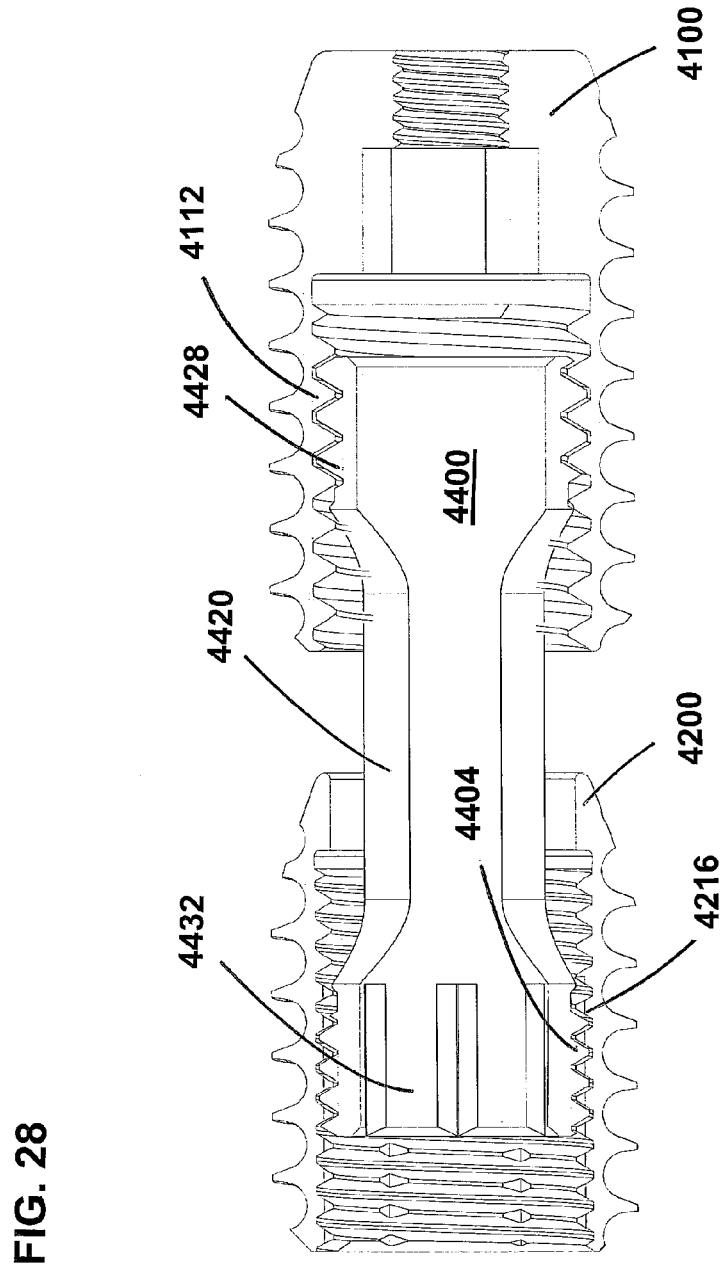
FIG. 28 is a cross section of a sub-assembly before the addition of the stabilization rod.

FIG. 28 shows a distal anchor 4100 with a threaded bore 4112 with a first thread pitch and a proximal anchor 4200 with a threaded bore 4216 with a second thread pitch which will typically be finer than the first thread pitch. Once the distal external thread 4428 of the dual threaded spanning distraction rod 4400 is engaged with the threaded bore 4112 of the distal anchor 4100 and the proximal external thread 4404 is engaged with the threaded bore 4216 of the proximal anchor 4200, application of torque to the driver engagement section 4432 will alter the distance between the distal anchor 4100 and the proximal anchor 4200. Rotation of the dual threaded spanning distraction rod 4400 in one direction will increase the distance between the anchors and rotation in the opposite direction will decrease the distance between anchors.

Figure 29:
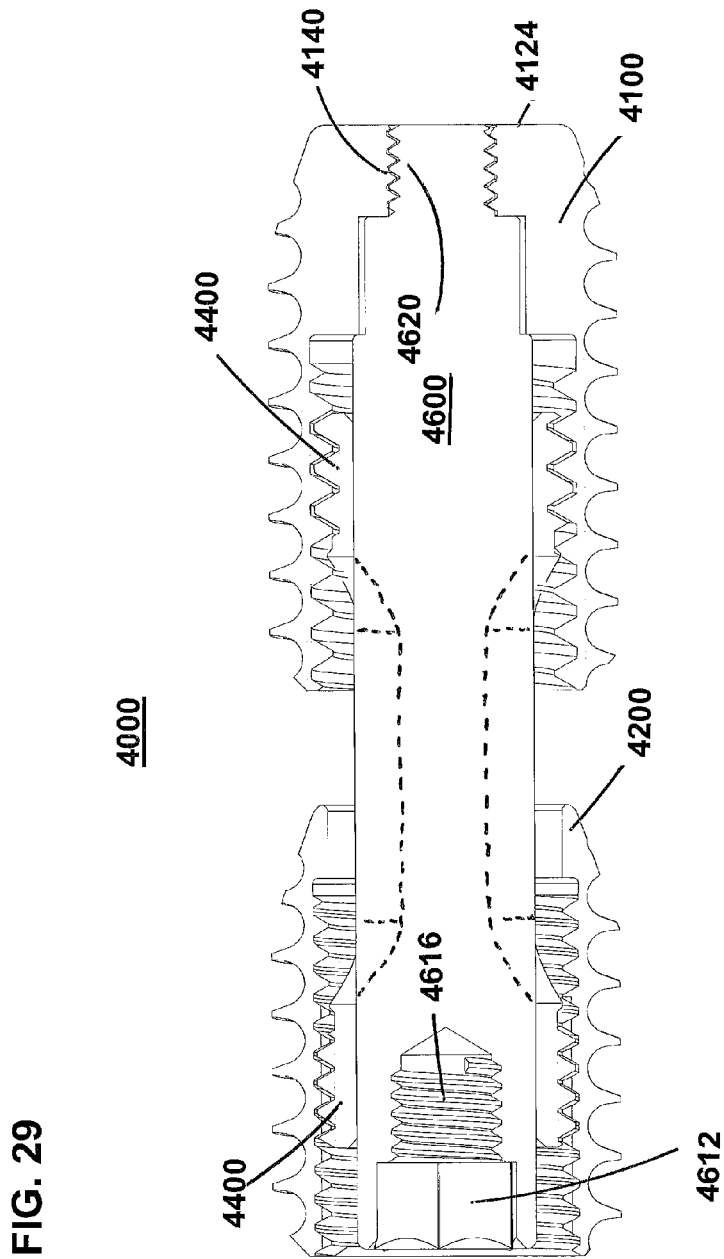
FIG. 29 is the cross section of a sub-assembly show in FIG. 28 after the addition of the stabilization rod.

FIG. 29 shows assembly 4000 with the addition of a stabilization rod 4600. The stabilization rod 4600 may be rotated by an appropriate driver through interaction with a driver engagement section 4612. The driver may use a retention rod to engage a threaded bore 4616. As the stabilization rod 4600 is rotated relative to the distal anchor 4100, an external thread 4620 on the stabilization rod 4600 engages an internal thread 4140 near the distal end 4124 of the distal anchor 4100.

The stabilization rod 4600 augments the structure of the dual threaded spanning distraction rod 4400 to compensate for the large ports 4420 (FIG. 28) and to block the large ports 4420 (FIG. 28) to prevent ingress of materials from the intervertebral disc space into the interior of assembly 4000. The stabilization rod 4600 lacks a shoulder or other feature to pull the proximal anchor 4200 towards the distal anchor 4100. The stabilization rod 4600 does not need a shoulder for that use as the dual threaded spanning distraction rod 4400 sets the distraction distance as the dual threaded spanning distraction rod 4400 has threaded engagement with both anchors.

The amount of distraction that may be imposed by the dual threaded spanning distraction rod 4400 will be a function of the difference in thread pitch between the distal external thread 4428 (FIG. 28) and the proximal external thread 4404 (FIG. 28) and the number of rotations that will be possible while both sets of threads are engaged with the anchors (4100 and 4200) before the dual threaded spanning distraction rod 4400 reaches the distal end of one or both anchors. Dual threaded spanning distraction rods 4400 having a particular thread pair ratio may be provided in a range of overall lengths so that the distal external thread 4428 (FIG. 28) may engage the distal anchor 4100 about the same time that the proximal external thread 4404 (FIG. 28) engages the proximal anchor 4200.

A procedure that calls for the imposition of a relatively large increase in the intervertebral disc height may use a dual threaded spanning distraction rod with a large difference in thread pitches in order to increase the potential to impose distraction. The anchors will be selected to have the appropriate internal thread pitches to work with the thread pitches on the on dual threaded spanning distraction rod.

Figure 30:
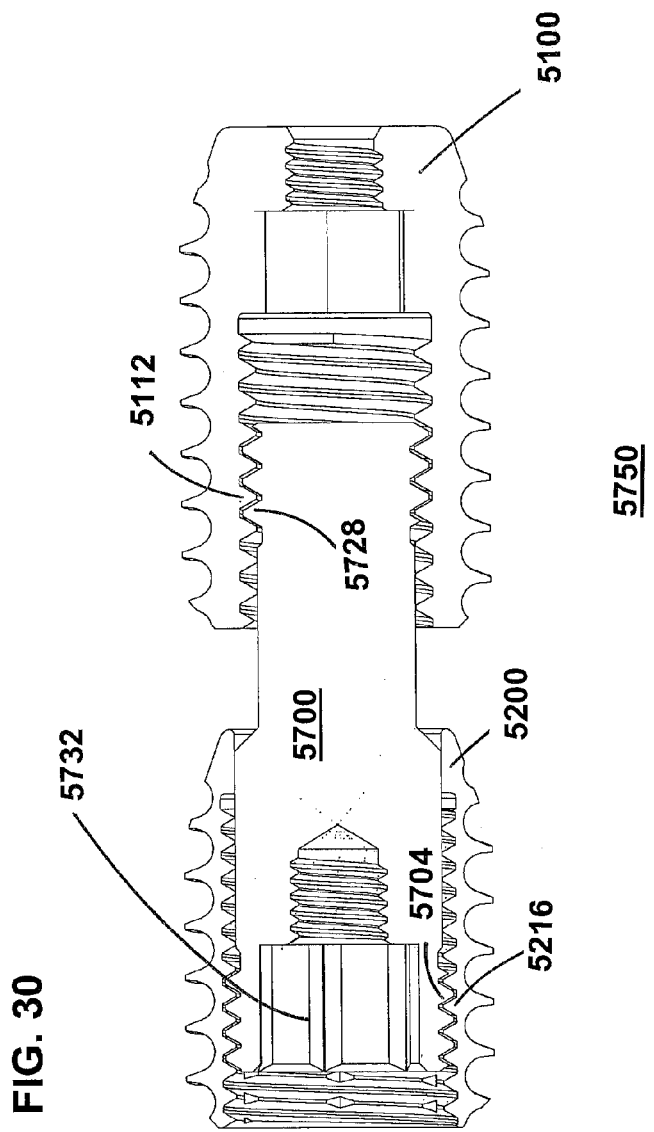
FIG. 30 is a cross section of an assembly with a dual threaded spanning distraction rod.

FIG. 30 shows assembly 5750 with distal anchor 5100 and proximal anchor 5200. Note that the threaded bore 5112 of the distal anchor 5100 has a smaller diameter than does threaded bore 5216. Instead of dual threaded spanning distraction rod 4400 and stabilization rod 4600, assembly 5750 has only a dual threaded spanning distraction rod 5700. As dual threaded spanning distraction rod 5700 does not have large ports 4420 (FIG. 28) there is not a need, nor is there room for a stabilization rod.

Dual threaded spanning distraction rod 5700 has a driver engagement section 5732, proximal external thread 5704 to engage the threaded bore 5216 of the proximal anchor 5200, and a distal external thread 5728 to engage the threaded bore 5112 of the distal anchor 5100 after passing through the center of threaded bore 5216. The imposition and reduction of distraction using the dual threaded spanning distraction rod 5700 operates in the same manner as the dual threaded spanning distraction rod 4400 (FIG. 29). The primary difference being that dual threaded spanning distraction rod 4700 cannot be used to deliver material to the intervertebral disc space. Thus, material must be delivered via trans-sacral access before the addition of dual threaded spanning distraction rod 5700 (and possibly before the delivery of one or both anchors) or material must be delivered by a non-trans-sacral access route.

Material Choices

While dual threaded spanning distraction rod 4700 may be fabricated from a relatively rigid biocompatible material such as titanium, other materials may be selected. A designer may opt to make all or at least the portion of the dual threaded spanning distraction rod between the threaded sections out of a material that is not as stiff as titanium. The material chosen may be selected as having mechanical properties that partially emulate the properties of cancellous bone. One choice is PEEK (polyaryletheretherketone). While Young's Modulus for cancellous bone is substantially less than Young's Modulus for PEEK, the value for PEEK is much closer than the Young's Modulus for titanium. Thus, PEEK is apt to behave more like cancellous bone than is titanium. Young's Modulus values for titanium alloys, PEEK, and cancellous bone are: 105-120 GPa, 3700 MPa, and 100 MPa.

The material chosen may actually have a Young's Modulus less than cancellous bone, particularly if the material was used in a spring or other structure to alter the effective mechanical properties.

Alternatives, Options, and Variations

The driver engagement sections shown as hexagonal sockets could be made in some other shape. The concave rounded segments of the hex sockets could be made with another shape sufficient to orient a driver and to preclude a driver not provided with that shape (or with the full set of shapes needed to interact with two or more special faces) from being inserted into the driver engagement section.

The fluted pattern shown in FIG. 8 and FIG. 10 could be replaced with some other pattern that reduces the surface contact between the distal portion of the spanning distraction rod and the component with which it engages. The pattern would not have to be symmetrical.

While the examples given above used one external thread in each threaded segment, those of skill in the art are aware that a rod may be created with two or more helical threads. Nothing in this disclosure precludes the use of two or more helical threads.

The dimensions and the proportions of the dimensions of the components could be changed to accommodate the specific needs of the surgery including modifications needed for the location in the spine receiving therapy and the size of the vertebrae such as the sizes found in an unusually large or small patient or in an animal receiving spine therapy.

One of skill in the art will recognize that some of the alternative implementations set forth above are not universally mutually exclusive and that in some cases additional implementations can be created that employ aspects of two or more of the variations described above. Likewise, the present disclosure is not limited to the specific examples or particular embodiments provided to promote understanding of the various teachings of the present disclosure. Moreover, the scope of the claims which follow covers the range of variations, modifications, and substitutes for the components described herein as would be known to those of skill in the art.

To assist the reader and for the sake of completeness, several applications or patents have been referenced. While these earlier applications have been incorporated by reference to provide additional detail it should be noted that these other applications (including those that have subsequently issued as patents) were written at an earlier time and had a different focus from the present application. Thus, to the extent that the teachings or use of terminology differ in any of these incorporated applications from the present application, the present application controls.

The legal limitations of the scope of the claimed invention are set forth in the claims that follow and extend to cover their legal equivalents. Those unfamiliar with the legal tests for equivalency should consult a person registered to practice before the patent authority which granted this patent such as the United States Patent and Trademark Office or its counterpart.

What is claimed is:

1. An assembly for implantation across two spinal vertebrae comprising:
   an externally threaded distal anchor for engagement with a distal vertebra;
   an externally threaded proximal anchor for engagement with a proximal vertebra;
   a spanning component that is threadedly engaged with the proximal anchor and extends into an interior of the distal anchor, wherein the spanning component may be rotated to set a minimum distance between a distal end of the proximal anchor and a proximal end of the distal anchor; and
   a compression inducing element adapted to:
      extend into an open interior of the spanning component;
      engage a shoulder within an interior of the proximal anchor, the shoulder facing a proximal end of the proximal anchor;
      engage a threaded bore within an interior of the distal anchor; and
      receive rotational input at a driver engagement section at a proximal end of the compression inducing element accessible via a proximal end of the proximal anchor such that a driver engaged with the driver engagement section of the compression inducing element has a capacity to reduce a distance between the distal anchor and the proximal anchor by pulling the distal anchor towards the proximal anchor, and wherein the shoulder within the interior of the proximal anchor is part of a component threadedly engaged to the interior of the proximal anchor.

2. The assembly of claim 1 wherein the spanning component imposes the minimum distance between the distal anchor and the proximal anchor, the minimum distance selected from a range of different possible minimum distances enabled by a capacity of the spanning component to move via threaded engagement relative to a threaded portion of the interior of the proximal anchor.

3. The assembly of claim 2 where the range of different possible minimum distances is broad enough to allow imposition of a hyper-distraction distance between the distal anchor and the proximal anchor to allow delivery of material into a hyper-distracted space between the distal vertebra and the proximal vertebra before using the compression inducing element to reduce the distance between the distal anchor and the proximal anchor and thus reduce the distance between the distal vertebra and the proximal vertebra.

4. The assembly of claim 2 wherein the compression inducing element limits the distance between the distal anchor and the proximal anchor to not exceed the minimum distance imposed by the spanning component.

5. The assembly of claim 1 wherein the distal anchor is adapted to engage two adjacent vertebrae.

6. The assembly of claim 5 where the distal anchor is adapted to distract an intervertebral disc space between the two adjacent vertebrae through a use of dissimilar thread pitch.

7. The assembly of claim 1 wherein a portion of the spanning component extending into the interior of the distal anchor is fluted to reduce contact area between the spanning component and the distal anchor.

8. The assembly of claim 1 wherein a portion of the spanning component extending into the interior of the distal anchor is adapted to reduce surface contact between the portion of the spanning component and the interior of the distal anchor.

9. The assembly of claim 1 wherein the spanning component has at least one lateral port in fluid communication with a proximal end of the spanning component so that the spanning component may be used as a conduit to deliver material between the distal vertebra and the proximal vertebra.

10. The assembly of claim 1 wherein:
   the spanning component has a spanning component driver engagement section at a distal end;
   the distal anchor has a distal anchor driver engagement section at a proximal end; and
   the spanning component driver engagement section has a relationship with the distal anchor driver engagement section such that one driver tip could be inserted from the proximal end to simultaneously engage both the spanning component driver engagement section and the distal anchor driver engagement section to allow both to be torqued, and wherein another driver tip could be used that would be capable to engage the spanning component driver engagement section but not the distal anchor driver engagement section such that the spanning component may be rotated without driving the distal anchor.

11. The assembly of claim 1 wherein the proximal vertebra is a portion of a sacrum.

12. The assembly of claim 1 wherein a proximal end of the proximal anchor is adapted to engage a counter-torque tube.

13. An assembly for implantation across two spinal vertebrae comprising:
   an externally threaded distal anchor for engagement with a distal vertebra;
   an externally threaded proximal anchor for engagement with a proximal vertebra;
   a spanning component that is threadedly engaged with the proximal anchor and extends into an interior of the distal anchor, the spanning component may be rotated to set a minimum distance between a distal end of the proximal anchor and a proximal end of the distal anchor; and
   a compression inducing element adapted to:
   extend into an open interior of the spanning component;
   engage a shoulder within an interior of the proximal anchor, the shoulder facing a proximal end of the proximal anchor; and
   threadedly engage an interior of the distal anchor such that rotation of the compression inducing element while threadedly engaged with the interior of the distal anchor has a capacity to reduce a distance between the distal anchor and the proximal anchor, and wherein the shoulder within the interior of the proximal anchor is part of a component threadedly engaged to the interior of the proximal anchor.

14. The assembly of claim 13 wherein the spanning component imposes the minimum distance between the distal anchor and the proximal anchor, the minimum distance selected from a range of different possible minimum distances enabled by a capacity of the spanning component to move via threaded engagement relative to a threaded portion of the interior of the proximal anchor.

15. The assembly of claim 14 where the range of different possible minimum distances is broad enough to allow imposition of a hyper-distraction distance between the distal anchor and the proximal anchor to allow delivery of material into a hyper-distracted space between the distal vertebra and the proximal vertebra before using the compression inducing element to reduce the distance between the distal anchor and the proximal anchor and thus reduce the distance between the distal vertebra and the proximal vertebra.

16. The assembly of claim 14 wherein the compression inducing element limits the distance between the distal anchor and the proximal anchor to not exceed the minimum distance imposed by the spanning component.

17. The assembly of claim 13 wherein the distal anchor is adapted to engage two adjacent vertebrae.

18. The assembly of claim 17 where the distal anchor is adapted to distract an intervertebral disc space between the two adjacent vertebrae through a use of dissimilar thread pitch.

19. The assembly of claim 13 wherein a portion of the spanning component extending into the interior of the distal anchor is fluted to reduce contact area between the spanning component and the distal anchor.

20. The assembly of claim 13 wherein a portion of the spanning component extending into the interior of the distal anchor is adapted to reduce surface contact between the portion of the spanning component and the interior of the distal anchor.

21. The assembly of claim 13 wherein the spanning component has at least one lateral port in fluid communication with a proximal end of the spanning component so that the spanning component may be used as a conduit to deliver material between the distal vertebra and the proximal vertebra.

22. The assembly of claim 13 wherein:
the spanning component has a spanning component driver engagement section at a distal end;
the distal anchor has a distal anchor driver engagement section at a proximal end; and
the spanning component driver engagement section has a relationship with the distal anchor driver engagement section such that one driver tip could be inserted from the proximal end to simultaneously engage both the spanning component driver engagement section and the distal anchor driver engagement section to allow both to be torqued, and wherein another driver tip could be used that would be capable to engage the spanning component driver engagement section but not the distal anchor driver engagement section such that the spanning component may be rotated without driving the distal anchor.

23. The assembly of claim 13 wherein the proximal vertebra is a portion of a sacrum.

24. The assembly of claim 13 wherein a proximal end of the proximal anchor is adapted to engage a counter-torque tube.

25. An assembly for insertion across an intervertebral space in a spine via a trans-sacral access channel, the assembly comprising:
a distal anchor for threaded engagement with a more distal vertebral body;
a proximal anchor for threaded engagement with a more proximal vertebral body separated from the more distal vertebral body by an intervertebral disc space;
a spanning component with an external thread adapted to engage an internal thread within the proximal anchor so that a distal end of the spanning component can be selectively advanced beyond a distal end of the proximal anchor to limit movement of the distal anchor towards the proximal anchor; and
a compression inducing element with a distal end that passes through a bore in the spanning component and engages a threaded bore in the distal anchor, the compression inducing element having a distal facing shoulder which engages a proximal facing shoulder within the proximal anchor so that rotation of the compression inducing element draws the distal anchor towards the proximal anchor to decrease distraction of the intervertebral space by decreasing a distance between the distal anchor and the proximal anchor until limited by the spanning component.

26. The assembly of claim 25 wherein the spanning component imposes a minimum distance between the distal anchor and the proximal anchor, the minimum distance selected from a range of different possible minimum distances enabled by a capacity of the spanning component to move via threaded engagement relative to a threaded portion of an interior of the proximal anchor.

27. The assembly of claim 26 where the range of different possible minimum distances is broad enough to allow imposition of a hyper-distraction distance between the distal anchor and the proximal anchor to allow delivery of material into a hyper-distracted space between the distal vertebra and the proximal vertebra before using the compression inducing element to reduce the distance between the distal anchor and the proximal anchor and thus reduce the distance between the distal vertebra and the proximal vertebra.

28. The assembly of claim 26 wherein the compression inducing element limits the distance between the distal anchor and the proximal anchor to not exceed the minimum distance imposed by the spanning component.

29. The assembly of claim 25 wherein the distal anchor is adapted to engage two adjacent vertebrae.

30. The assembly of claim 29 where the distal anchor is adapted to distract an intervertebral disc space between the two adjacent vertebrae through a use of dissimilar thread pitch.

31. The assembly of claim 25 wherein a portion of the spanning component extending into an interior of the distal anchor is fluted to reduce contact area between the spanning component and the distal anchor.

32. The assembly of claim 25 wherein a portion of the spanning component extending into an interior of the distal anchor is adapted to reduce surface contact between the portion of the spanning component and an interior of the distal anchor.

33. The assembly of claim 25 wherein the spanning component has at least one lateral port in fluid communication with a proximal end of the spanning component so that the spanning component may be used as a conduit to deliver material between the distal vertebra and the proximal vertebra.

34. The assembly of claim 25 wherein: the spanning component has a spanning component driver engagement section at a distal end; the distal anchor has a distal anchor driver engagement section at a proximal end; and the spanning component driver engagement section has a relationship with the distal anchor driver engagement section such that one driver tip could be inserted from the proximal end to simultaneously engage both the spanning component driver engagement section and the distal anchor driver engagement section to allow both to be torqued, and wherein another driver tip could be used to engage the spanning component driver engagement section but not the distal anchor driver engagement section such that the spanning component may be rotated without driving the distal anchor.

35. The assembly of claim 25 wherein the proximal vertebra is a portion of a sacrum.

36. The assembly of claim 25 wherein a proximal end of the proximal anchor is adapted to engage a counter-torque tube.

\* \* \* \* \*